(12) United States Patent
Mallinson

(10) Patent No.: US 11,752,295 B2
(45) Date of Patent: Sep. 12, 2023

(54) METHOD AND SYSTEM FOR CLASSIFYING VIRTUAL REALITY (VR) CONTENT BASED ON MODELED DISCOMFORT OF A USER

(71) Applicant: Sony Interactive Entertainment Inc., Tokyo (JP)

(72) Inventor: Dominic S. Mallinson, Redwood City, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 738 days.

(21) Appl. No.: 15/366,624

(22) Filed: Dec. 1, 2016

(65) Prior Publication Data
US 2018/0096244 A1 Apr. 5, 2018

Related U.S. Application Data

(60) Provisional application No. 62/402,377, filed on Sep. 30, 2016.

(51) Int. Cl.
*G06N 3/08* (2023.01)
*A61M 21/00* (2006.01)
(Continued)

(52) U.S. Cl.
CPC ............. *A61M 21/00* (2013.01); *G06F 3/011* (2013.01); *G06F 3/012* (2013.01); *G06F 18/22* (2023.01);
(Continued)

(58) Field of Classification Search
CPC .. G06N 3/08; G06N 3/02; G06N 5/04; H04N 13/366; A61M 21/00; G06F 3/012;
(Continued)

(56) References Cited

U.S. PATENT DOCUMENTS 5,694,939 A * 12/1997 Cowings .............. A61B 5/6804
 600/27
8,708,884 B1 * 4/2014 Smyth .................. A61M 21/00
 600/27

(Continued)

OTHER PUBLICATIONS

The Authoritative Dictionary of IEEE Standard Terms, pp. 870-871 (7th ed. 2000) (Year: 2000).*

(Continued)

*Primary Examiner* — Kakali Chaki
*Assistant Examiner* — Kevin L. Smith
(74) *Attorney, Agent, or Firm* — PENILLA IP, APC

(57) ABSTRACT

A method for method for classification of virtual reality (VR) content for use in head mounted displays (HMDs). The method includes accessing a model that identifies a plurality of learned patterns associated with the generation of corresponding baseline VR content that is likely to cause discomfort. The method includes executing a first application to generate first VR content. The method includes extracting data associated with simulated user interactions with the first VR content, the extracted data generated during execution of the first application. The method includes comparing the extracted data to the model to identify one or more patterns in the extracted data matching at least one of the learned patterns from the model such that the one or more patterns are likely to cause discomfort.

19 Claims, 12 Drawing Sheets

(51) Int. Cl.
| | |
|---|---|
| *H04N 13/366* | (2018.01) |
| *G06F 3/01* | (2006.01) |
| *G06F 18/22* | (2023.01) |
| *G06F 18/24* | (2023.01) |
| *G06T 19/00* | (2011.01) |

(52) U.S. Cl.
CPC ............... *G06F 18/24* (2023.01); *G06N 3/08* (2013.01); *G06T 19/006* (2013.01); *H04N 13/366* (2018.05); *A61M 2021/005* (2013.01); *A61M 2021/0044* (2013.01); *A61M 2205/507* (2013.01); *H04N 2213/002* (2013.01)

(58) Field of Classification Search
CPC ...... G06K 9/6201; G06K 9/6267; G06K 9/66; G06T 19/006
See application file for complete search history.

(56) References Cited

U.S. PATENT DOCUMENTS

| | | | | |
|---|---|---|---|---|
| 9,104,867 | B1* | 8/2015 | Thioux | G06F 21/56 |
| 2003/0073922 | A1* | 4/2003 | Miller | H04N 1/00 |
| | | | | 600/545 |
| 2011/0028805 | A1* | 2/2011 | Yamazaki | H04N 13/359 |
| | | | | 600/307 |
| 2012/0036004 | A1* | 2/2012 | Pradeep | A61B 5/04842 |
| | | | | 705/14.41 |
| 2012/0134543 | A1 | 5/2012 | Fedorovskaya et al. | |
| 2013/0128012 | A1* | 5/2013 | Turner | G06F 3/011 |
| | | | | 348/E13.041 |
| 2013/0241955 | A1* | 9/2013 | Tamaru | H04N 13/344 |
| | | | | 345/633 |
| 2014/0268356 | A1 | 9/2014 | Bolas et al. | |
| 2015/0309316 | A1* | 10/2015 | Osterhout | G06F 3/0488 |
| | | | | 345/8 |
| 2016/0077547 | A1* | 3/2016 | Aimone | A61B 5/1114 |
| | | | | 345/8 |
| 2016/0262608 | A1* | 9/2016 | Krueger | A61B 3/0041 |
| 2017/0212829 | A1* | 7/2017 | Bales | G06F 11/3604 |

OTHER PUBLICATIONS

Kempka et al., "ViZDoom: A Doom-based AI Research Platform for Visual Reinforcement Learning," IEEE Conf. on Computational Intelligence & Games (Sep. 20-23, 2016) (Year: 2016).*

Julie Drexler, "Identification Of System Design Features That Affect Sickness In Virtual Environments," University of Central Florida (2005) (Dissertation) (Year: 2005).*

Jiang et al., "A Depth Perception and Visual Comfort Guided Computational Model for Stereoscopic 3D Visual Saliency," Signal Processing: Image Comm'n (2015) (Year: 2015).*

James E. Russell, "Multiple Model Adaptive Estimation and Head Motion Tracking in a virtual Environment: An Engineering Approach," Air Force Institute of Technology (1994) (Year: 1994).*

Julie Drexler, "Identification Of System Design Features That Affect Sickness In Virtual Environments," University of Florida (2006) (Thesis) (Year: 2006).*

Jung et al., "VENUS: The Online Game Simulator using Massively Virtual Clients," Springer-Verlag (2005) (Year: 2005).*

Ajoy S Fernandes et al, Combating VR Sickness through Subtle Dynamic Field-Of-View Modification, 2016 IEEE Symposium on 3D User Interfaces (3DUI), Mar. 1, 2016 (Mar. 1, 2016), pp. 201-210, XP055439351, DOI: 10.1109/3DUI.2016.7460053, ISBN: 978-1-5090-0842-1.

International Search Report and Written Opinion, PCT/US2017/046827, dated Jan. 22, 2018, 14 pages.

* cited by examiner

METHOD AND SYSTEM FOR CLASSIFYING VIRTUAL REALITY (VR) CONTENT BASED ON MODELED DISCOMFORT OF A USER

CROSS REFERENCE TO RELATED APPLICATIONS

The present application claims priority to and the benefit of the commonly owned, provisional patent application, U.S. Ser. No. 62/402,377, entitled "METHOD AND SYSTEM FOR CLASSIFYING VIRTUAL REALITY (VR) CONTENT BASED ON MODELED DISCOMFORT OF A USER WHEN INTERACTING WITH THE VR CONTENT," with filing date Sep. 30, 2016, which is herein incorporated by reference in its entirety.

This application is related to commonly assigned, co-pending U.S. patent application Ser. No. 15/085,899, entitled "PERSONALIZED DATA DRIVEN GAME TRAINING SYSTEM," filed on Mar. 30, 2016, the disclosure of which is hereby incorporated by reference in its entirety.

TECHNICAL FIELD

The present disclosure is related to improving user experience when interacting with virtual reality (VR) content, and the classification of VR content based on levels of discomfort. Among other things, this disclosure describes methods and systems for training a deep learning engine to build a model configured for classifying VR content according to predicted levels of discomfort associated with a typical or predetermined type of user interacting with the VR content, and wherein the model is also configured for classifying or calibrating a user according to tested levels of experienced discomfort.

BACKGROUND OF THE DISCLOSURE

Computer generated virtual reality (VR) allows a user to be immersed in a simulated real environment or an imaginary environment, for example. With complete immersion, the user is able to interact with the simulated or imaginary environment, as if the user were present within that VR environment. That is, the user is able to move and look around the VR environment, and possibly interact with objects within that VR environment.

VR systems can use some display system to let the user view the VR environment. These display systems may include a computer monitor or display screen that is presented in front of the user. When the display screen is smaller, the VR experience of the user is hampered by visual stimulation from the surrounding real environment (e.g., sunlight, objects in real space, etc.). The VR experience may be improved by increasing the display size to reduce the influence of the surrounding real environment. Further, the display system may be designed to block out stimulation from the surrounding real environment. For example, a head mounted display (HMD) worn by a user is able to block out light from the physical, real environment, and present a stereoscopic screening system to the user for viewing the VR environment in three dimensions (3D). These HMDs may include viewing goggles integrated with a mounting system that is worn on or over the head. Still other more complex VR systems may be integrated with movement sensors that allow a user to make moves in a real world that may then be translated in some form to the world of VR. For instance, hand gestures/movements may be used to interact with VR objects, and moving through the real world (e.g., walking in the physical environment) may be translated to similar movement in the VR environment (e.g., walking or running in the VR environment).

VR systems have been embraced by various industries, such as the military, real estate, medicine, video gaming, etc. Because the user can be totally immersed within a VR environment, that VR environment may simulate a real environment for purposes of training, enjoyment, and escape. For example, a VR system may be used for pilot training in the military, surgical technique training within the medical industry, showing a listing by a real estate agent, or experiencing a vacation destination. In addition, the VR environment may be used to simulate a completely imaginary environment, such as a fantasy world where characters have super human powers. For example, the user may be immersed within a video gaming VR environment that allows the user to take on the skills and movements of a gaming character within that VR environment. In that manner, the user is able to extend the margins of reality by giving the user the sense of imaginary movements and skills. This is analogous to having a disabled person feel as if he or she were able to move (e.g., walk) within the VR environment.

However, the VR experience of a user will vary with the type of VR content presented, and with the compatibility of the user for interacting with the VR content. In some cases, VR content may induce sickness or discomfort in the user that is akin to motion sickness experienced in the physical, real world. The discomfort by the user may be due in general to sensory cues (e.g., visual, auditory, etc.) that are somehow not compatible with a specific user, though research in the area has not determined exactly why these cues may or may not be compatible. Further, because it is unknown why VR content may induce discomfort by a specific user, it is difficult to predict whether VR content will induce user discomfort, or whether a user is susceptible to discomfort when interacting with specific VR content.

It is in this context that embodiments of the disclosure arise.

SUMMARY

Embodiments of the present disclosure relate to systems and methods for building a model through a deep learning engine that is configured for predicting discomfort of a user when interacting with VR content, and for classifying VR content based on predicted discomfort of a user as determined by the model, and for using the model or a corresponding form of the model to classify users based on experienced discomfort when tested. Several inventive embodiments of the present disclosure are described below.

In one embodiment, a method for classification of virtual reality (VR) content for use in head mounted displays (HMDs) is disclosed. The method includes accessing a model that identifies a plurality of learned patterns associated with the generation of corresponding baseline VR content that is likely to cause discomfort. The method includes executing a first application to generate first VR content. The method includes extracting data associated with simulated user interactions with the first VR content, the extracted data generated during execution of the first application. The method includes comparing the extracted data to the model to identify one or more patterns in the extracted data matching at least one of the learned patterns from the model such that the one or more patterns are likely to cause discomfort Further, the model is generated by applying deep learning techniques. In one embodiment, the deep learning technique disclosed includes executing a plurality of testing applications for interaction by a plurality of testers to generate a plurality of baseline VR content. The deep learning technique includes extracting testing data associated with tester interactions with the baseline VR content, the extracted data generated during execution of the plurality of testing applications. The deep learning technique includes monitoring physiological measurements of the plurality of testers when interacting with the plurality of baseline VR content, wherein the plurality of baseline VR content is associated with a plurality of baseline discomfort reactions, wherein known patterns of physiological measurements are associated with expected discomfort reactions. The deep learning technique includes applying the physiological measurements and the extracted testing data associated with tester interactions to a deep learning engine. The deep learning technique includes correlating the physiological measurements and the extracted testing data associated with tester interactions to determine the plurality of learned patterns that are likely to produce discomfort experiences in the testers based on physiological measurements that align with the plurality of baseline discomfort reactions. Further, the model outputs a corresponding set of discomfort experiences for corresponding content. The deep learning technique includes correlating a plurality of sets of discomfort experiences with a plurality of levels of discomfort for the model.

In one embodiment, another method for classification of virtual reality (VR) content for use in HMDs is disclosed. The method includes accessing a model that identifies a plurality of learned patterns associated with the generation of corresponding baseline VR content that is likely to cause discomfort. The method includes processing a first application to generate data associated with simulated user interactions with first VR content of the first application. The method includes comparing the extracted data to the model to identify a pattern in the extracted data matching at least one of the learned patterns, such that the identified pattern is likely to cause discomfort.

Other aspects of the disclosure will become apparent from the following detailed description, taken in conjunction with the accompanying drawings, illustrating by way of example the principles of the disclosure.

BRIEF DESCRIPTION OF THE DRAWINGS

The disclosure may best be understood by reference to the following description taken in conjunction with the accompanying drawings in which.

DETAILED DESCRIPTION

Figure 1A:
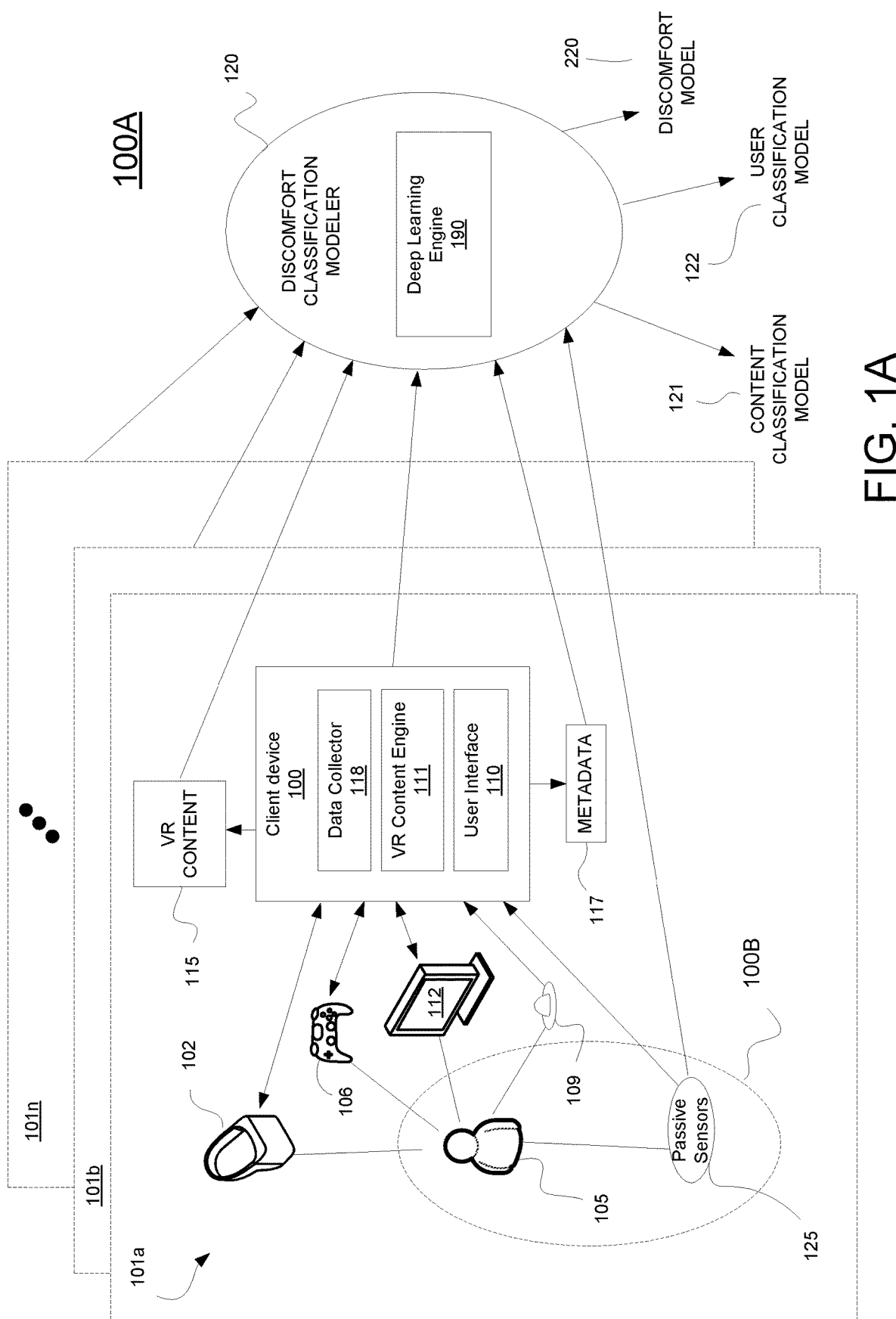
FIG. 1A illustrates a system used for building a discomfort and/or sickness recognition model through a deep learning engine that is configured for correlating discomfort of a user when interacting with VR content, in accordance with one embodiment of the present disclosure.

Although the following detailed description contains many specific details for the purposes of illustration, anyone of ordinary skill in the art will appreciate that many variations and alterations to the following details are within the scope of the present disclosure. Accordingly, the aspects of the present disclosure described below are set forth without any loss of generality to, and without imposing limitations upon, the claims that follow this description.

Generally speaking, the various embodiments of the present disclosure describe systems and methods implementing deep learning techniques to determine which VR content induces user discomfort and/or sickness, and for building a model to classify VR content based on predicted user discomfort and/or sickness, and for building a model to classify users based on personalized determinations (e.g., tested) of user discomfort and/or sickness when viewing VR content. In particular, embodiments of the present disclosure use physiological measurements (e.g., galvanic skin resistance, brain waves, alpha brain waves, heart rate, eye gaze, head motion, electrogastrography, etc.) of content testers as inputs to a deep learning engine. For example, when the testers interact with VR content (e.g., play a gaming application), the physiological data is recorded along with data from the VR content (e.g., visual data). The deep learning engine looks at in-game features (e.g., horizon, avatar linear and rotational accelerations, gravity motion of objects [ballistics data having gravity influences], field of view, stereoscopy, latency, etc.) in order to correlate the VR game generated measurements (based on the in-game features) with the physiological measurements.

Accordingly, embodiments of the present disclosure provide for learning which VR content or patterns of VR content will induce discomfort and/or sickness in users. With this knowledge, a user can be classified based on predicted levels of discomfort that user will experience when viewing VR content in embodiments. This provides for targeted content delivery (e.g., VR content, advertising, etc.) to users, such as providing content to users who avoid VR content classified as inducing discomfort and/or sickness for that user. Further, with that knowledge, VR content can be classified based on the predicted discomfort that is associated with patterns contained in the VR content in embodiments. That classification can be used to provide notification to prospective users (e.g., customers), wherein the notification indicates what type of discomfort may be experienced when viewing corresponding VR content. In addition, that classification may be used during the development phase of VR content to make sure that the determined classification matches a designed classification. For example, a mismatch occurs when there is a technological problem in the VR content (e.g., code, etc.), or when the VR content contains material that induces discomfort and/or sickness that does not match targeted discomfort and/or sickness reactions. In that manner, VR content can be designed for targeted users that fit a specific profile associated with similar discomfort and/or sickness reactions when viewing VR content, and tested throughout the design cycle to ensure that the VR content remains targeted to those users. Also, the generation and design of VR content is improved by providing a way to test VR content to discover technical flaws in the VR content that is evidenced by a corresponding mismatch between expected/designed and tested discomfort and/or sickness.

Embodiments of the present invention are described within the context of playing gaming applications to generate VR content; however, it is understood that VR content is not limited to gaming applications and encompasses any type of VR content obtained from any source (e.g., video, application, etc.).

With the above general understanding of the various embodiments, example details of the embodiments will now be described with reference to the various drawings.

FIG. 1A illustrates a system 100A used for building a discomfort and/or sickness recognition model through a deep learning engine that is configured for correlating discomfort of a user when interacting with VR content, in accordance with one embodiment of the present disclosure. System 100A can be implemented in a testing environment in order to learn under what conditions users will experience discomfort and/or sickness when viewing and/or interacting with VR content, and then to apply that knowledge to build models that can be used to classify VR content based on predicted discomfort and/or sickness experienced by users when interacting with the VR content, and to classify a user based on tested discomfort and/or sickness responses when interacting with test VR content. The user classification can be aligned with the VR content classification in order to give a corresponding user the best experience when interacting with VR content.

The testing environment includes a plurality of test users that is subjected to a plurality of VR content. Each of the test users is monitored using a corresponding test system. For illustration, test user 105 is monitored using test system 101a, and other test users are monitored using test systems 101b-101n, etc.

As a representative example of the plurality of test systems (e.g., 101a-101n), test system 101a is described to illustrate the monitoring of the test user 105 during interaction with VR content 115. The VR content 115 includes one or more baseline VR content, wherein each baseline content is associated with known or true discomfort and/or sickness responses. Further, the VR content may be of any type, including rendered images from gaming applications, videos, multimedia content, static images, etc.

Client device 100 is configured for generating the VR content 115. For example, the VR content may be generated by an application (e.g., gaming application) running on the VR content engine 111 (e.g., game execution engine). For example, the application is designed to produce images that when viewed through a corresponding display device (e.g., HMD 102 or display 112) can give a user a three-dimensional VR viewing experience. In one implementation, the client device 100 may be a stand-alone system configured to generate and/or play the VR content (e.g., execute the code of a gaming application to render images), or may request access to VR content over a network (not shown), such as the internet, or for rendering VR content received from an instance of an application (e.g., gaming application) executed by a back end server (e.g., implementing a virtual machine), and delivered to the display device 112 associated with user 105, or delivered to a head mounted display (HMD) 102 that is configured to display VR content. In some embodiments, the client device 100 may be an HMD.

Further, the client device 100 may receive input from various types of input devices, such as game controllers 106, tablet computers, keyboards, gestures captured by video cameras, mice, touch pads, etc. Client device 100 can be any type of computing device having at least a memory and a processor module that is capable of generating and/or playing the VR content 115. Some examples of client device 100 include a personal computer (PC), a game console, HMD, a home theater device, a general purpose computer, a video recording player, mobile computing device, a tablet, a phone, or any other types of computing devices that can play the VR content 115. User interface 110 may be used for playing the VR content, setting up testing, and/or used for managing the collection of data input into the discomfort classification modeler 120.

In particular, client device 100 is configured for generating and/or receiving rendered images of VR content, and for displaying the rendered images on display 112 or HMD 102. For example, the rendered images may be associated with an instance of a gaming application executing on the client device 100, or executing on a back end game server in association with user 105. In the case of interactive VR content, such as that associated with a gaming application, client device 100 is configured to interact with the instance of the video game executing on engine 111 and that is associated with game play of user 105, such as through input commands that are used to drive game play.

During the interaction by user 105 with the VR content 115, various data is monitored, wherein the data is associated with the VR content 115 (e.g., rendered images, etc.)

and the user 105. The data may be monitored and collected by client device 100, or directly by the discomfort classification modeler 120. This data is input in the discomfort classification modeler 120 in order to learn the VR content and/or patterns of VR content that induce discomfort and/or sickness in users. The data includes VR content that is generated, For example, the VR content is monitored by test system 101*a* to recognize patterns associated with VR content that can then be correlated with data from test users that experience discomfort and/or sickness, wherein a pattern can include any type of VR content (e.g., static image, sequence of images, etc.), or patterns of actions taken or generated by the user in association with the generation of that VR content. The patterns may be associated with simulated user interactions with corresponding VR content. Over time, if the same pattern of VR content (e.g., moving horizon, etc.), or patterns of actions, consistently induces discomfort and/or sickness in the test users, then those patterns can be labeled as producing discomfort and/or sickness reactions in consumer users who interact with that VR content. In one embodiment, the client device 100 is configured to monitor and parse out the patterns of VR content, or patterns of actions taken or generated by the user in association with the generation of that VR content, while the VR content is being played or interacted with by the test user 105. In another embodiment, the discomfort classification modeler 120, and more specifically, the deep learning engine 190 is configured to monitor and parse out the patterns of VR content, or patterns of actions taken or generated by the user in association with the generation of that VR content, while it is being played or interacted with by the test user 105.

In addition, the test system 101*a* monitors physiological data associated with the test user 105 collected during interaction with VR content 115. The physiological data may be passively or actively monitored. Passive monitoring does not require help from the user, whereas active monitoring requires user help.

In particular, in one embodiment test system 101*a* is configured to actively monitor physiological data, for example, through the use of actuator 109. For instance, as the test user 105 is interacting with VR content 115, when the test user is feeling discomfort and/or sickness, the user may actively engage the actuator 109 (e.g., push a button). The user may also be prompted to input the degree of discomfort/comfort and/or sickness felt during the interaction with VR content 115 at various times (e.g., periodic, random, specified, etc.) through user interface 110.

Figure 1B:
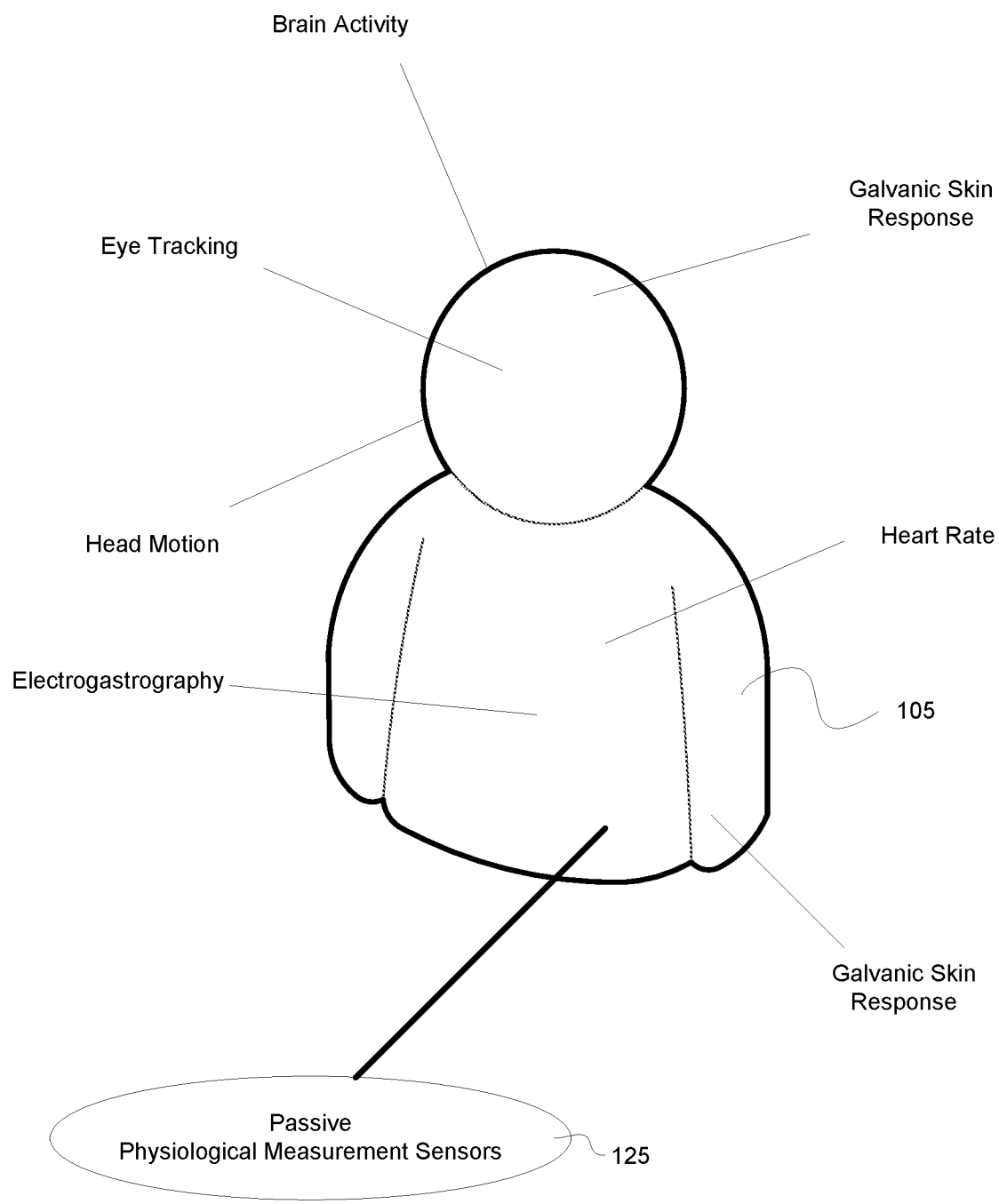
FIG. 1B illustrates a sensory system configured to passively monitor physiological responses and feedback of a test user when interacting with VR content, in accordance with one embodiment of the present disclosure.

In another embodiment sensors 125 passively monitor the physiological data while the test user 105 is interacting with VR content 115. FIG. 1B illustrates the passive monitoring by the sensors 125 of physiological responses and feedback of a test user 105 when interacting with VR content, in accordance with one embodiment of the present disclosure. For illustration, physiological data may include galvanic skin resistance, brain activity (e.g., alpha waves), heart rates, eye movement, head movement, electrogastrography, etc. For example, electrogastrography and galvanic skin resistance may measure the differences in electrical conductivity or characteristics of the skin and muscles. In particular, more sweating will provide better conductivity. Electrogastrography can measure the motility of the GI tract muscle contractions which gives a strong indication of nausea. It is possible that discomfort and/or sickness caused by certain patterns of VR content 115 (e.g., aerobatic air plane simulation) by the test user 105 may induce a change in the galvanic skin resistance, possibly due to an increase in sweating. Further, brain activity may be measured and recorded over time, to determine if there is some correlation between the measured brain activity and discomfort and/or sickness caused by certain patterns of VR content 115. It is also possible that discomfort and/or sickness may manifest itself in certain eye or head motions, both of which may exhibit slowness or abnormal movement. In addition, the heart rate may exhibit certain patterns when the test users are experiencing discomfort and/or sickness caused by interaction with VR content. Though one item of physiological data, or one type of physiological data may not provide a definitive value in terms of making a correlation between discomfort and/or sickness of a test user and patterns of VR content, over time the certain physiological data or combinations of different types of physiological data collected over many test cases of interactions of test users with VR content will produce more reliable correlations between discomfort and/or sickness and patterns of VR content.

Further, the test data collected in association with the VR content 115 and the physiological data from the test user 105 can be correlated, such that an association can be made between a specific pattern of VR content, or patterns of actions taken by the user in association with the VR content, and physiological reactions, wherein the VR content may induce a measured physiological reaction in the test user 105. For example, a time stamp may be collected in association with both the collected test data associated with the VR content 115 and the physiological data of test user 105, wherein data with corresponding and possibly lagging time stamps may be correlated with each other. In particular, discomfort classification modeler 120 is configured to learn what types and/or patterns of VR content, or patterns associated with the generation of or interaction with VR content, or patterns associated with simulated or tested user interactions with corresponding VR content, is likely to induce discomfort and/or sickness in a user. These identified patterns may be included within a discomfort model 220 that can be used to identify points in an application under test that might induce discomfort and/or sickness in a user. The discomfort classification modeler 120 is further described below in relation to FIGS. 1D-1F.

Figure 1C:
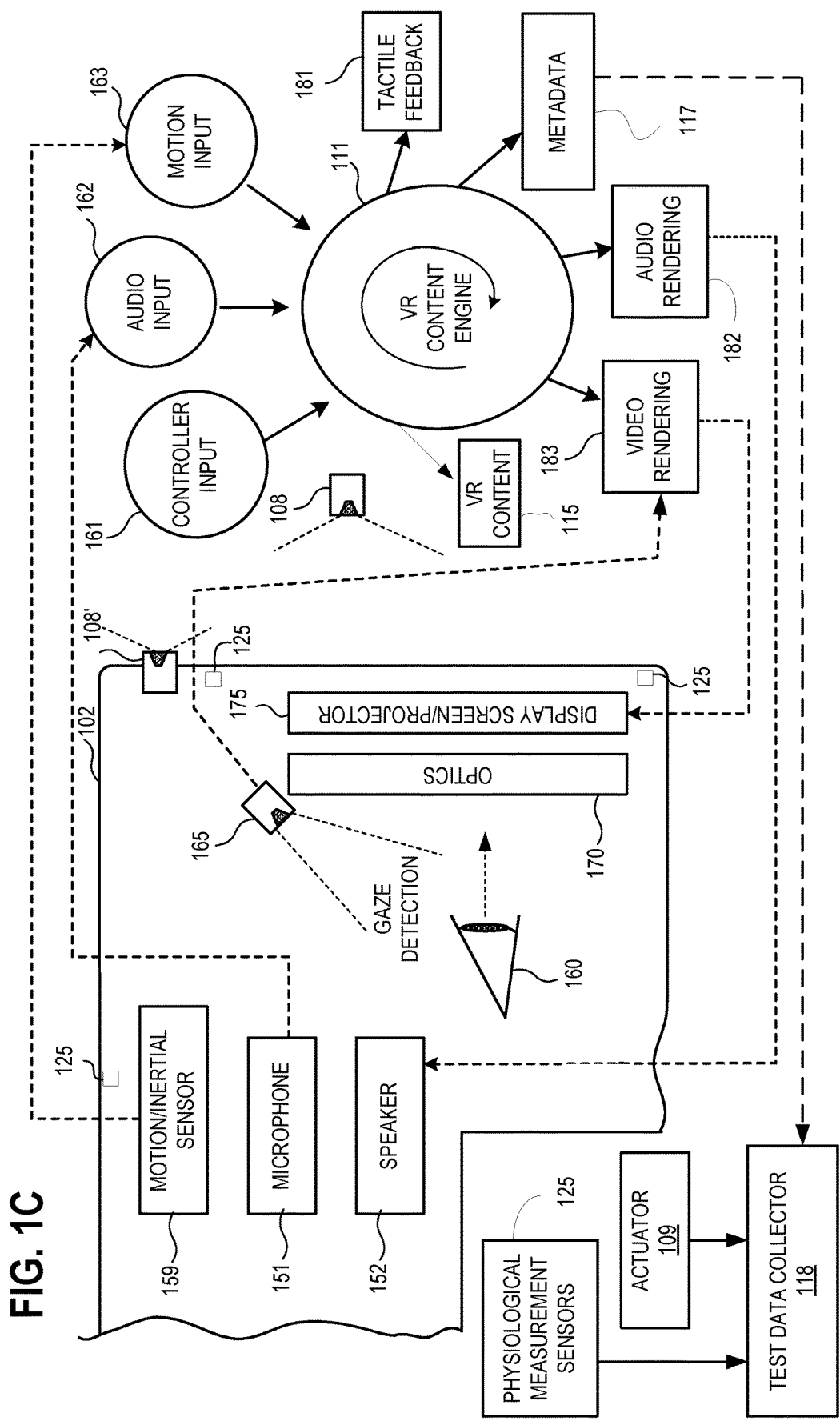
FIG. 1C conceptually illustrates the function of a HMD in conjunction with the execution of an application generating VR content, in accordance with an embodiment of the invention.

FIG. 1C conceptually illustrates the function of a HMD 102 in conjunction with the generation of VR content (e.g., execution of an application and/or video game, etc.) and the testing of VR content to determine patterns of VR content, or what actions taken or generated by the user in association with the generation of VR content, is likely to induce discomfort and/or sickness in a user, in accordance with an embodiment of the invention. Data collected in association with the generation of VR content 115 by the VR content engine 111 may be used for identification of VR content or patterns associated with VR content 115 that may induce user discomfort (e.g., nausea, motion sickness, etc.). In some implementations, the VR content engine 111 is being executed on a client device 100 (not shown) that is communicatively coupled to the HMD 102, as previously described. For example, the VR content engine 111 executing an application may be a gaming engine executing a video game, and is configured to receive inputs to update a game state of the video game. The gaming engine may be a gaming console, or back end gaming server, as previously described. The game state of the video game can be defined, at least in part, by values of various parameters of the video game which define various aspects of the current gameplay, such as the presence and location of objects, the conditions of a virtual environment, the triggering of events, user profiles, view perspectives, actions taken by the user 105, controller actions, gaze tracking information, etc.

In the illustrated embodiment, the VR content engine 111 receives, by way of example, controller input 161, audio input 162 and motion input 163. The controller input 161 may be defined from the operation of a gaming controller separate from the HMD 102, such as a hand-held gaming controller 104 (e.g., Sony DUALSHOCK®4 wireless controller, Sony PlayStation®Move motion controller) or wearable controllers, such as wearable glove interface controller, etc. By way of example, controller input 161 may include directional inputs, button presses, trigger activation, movements, gestures or other kinds of inputs processed from the operation of a gaming controller. The audio input 162 can be processed from a microphone 151 of the HMD 102, or from a microphone included in the image capture device 108 or elsewhere within the local system environment. The motion input 163 can be processed from a motion sensor 159 included in the HMD 102, or from image capture device 108 as it captures images of the HMD 102. For example, the motion sensor 159 may include an inertial sensor configured to capture acceleration data of the HMD 102 that is associated with head movement of the user 105. In addition, image capture device 108 may be configured for head tracking to monitor head movement of the user 105. The VR content engine 111 (e.g., executing a gaming application) receives inputs which are processed according to the configuration of the game engine to update the game state of the video game. The engine 111 outputs game state data to various rendering modules which process the game state data to define content which will be presented to the user 105.

In the illustrated embodiment, a video rendering module 183 is defined to render a video stream including VR content 115, which when presented on the HMD 102 gives a user 105 a three dimensional VR experience. A lens of optics 170 in the HMD 102 is configured for viewing the VR content 115. A display screen 175 is disposed behind the lens of optics 170, such that the lens of optics 170 is between the display screen 175 and an eye 160 of the user 105, when the HMD 102 is worn by the user 105. In that manner, the video stream may be presented by the display screen/projector mechanism 175, and viewed through optics 170 by the eye 160 of the user 105. An HMD user 105 may elect to interact with the interactive VR content (e.g., VR video source, video game content, etc.) by wearing the HMD and selecting a video game for game play, for example. Interactive virtual reality (VR) scenes from the video game are rendered on the display screen 175 of the HMD. In that manner, the HMD allows the user 105 to completely immerse in the game play by provisioning display mechanism of the HMD in close proximity to the user's eyes. The display regions defined in the display screen of the HMD for rendering content may occupy large portions or even the entirety of the field of view of the user 105. Typically, each eye is supported by an associated lens of optics 170 which is viewing one or more display screens.

An audio rendering module 182 is configured to render an audio stream for listening by the user 105. In one embodiment, the audio stream is output through a speaker 152 associated with the HMD 102. It should be appreciated that speaker 152 may take the form of an open air speaker, headphones, or any other kind of speaker capable of presenting audio.

In one embodiment, a gaze tracking camera 165 is included in the HMD 102 to enable tracking of the gaze of the user 105. Although only one gaze tracking camera 165 is included, it should be noted that more than one gaze tracking camera may be employed to track the gaze of the user 105. The gaze tracking camera captures images of the user's eyes, which are analyzed to determine the gaze direction of the user 105. In one embodiment, information about the gaze direction of the user 105 can be utilized to affect the video rendering. For example, if a user's eyes are determined to be looking in a specific direction, then the video rendering for that direction can be prioritized or emphasized, such as by providing greater detail or faster updates in the region where the user 105 is looking. It should be appreciated that the gaze direction of the user 105 can be defined relative to the head mounted display, relative to a real environment in which the user 105 is situated, and/or relative to a virtual environment that is being rendered on the head mounted display.

Broadly speaking, analysis of images captured by the gaze tracking camera 192, when considered alone, provides for a gaze direction of the user 105 relative to the HMD 102. However, when considered in combination with the tracked location and orientation of the HMD 102, a real-world gaze direction of the user 105 can be determined, as the location and orientation of the HMD 102 is synonymous with the location and orientation of the user's head.

That is, the real-world gaze direction of the user 105 can be determined from tracking the positional movements of the user's eyes and tracking the location and orientation of the HMD 102. When a view of a virtual environment is rendered on the HMD 102, the real-world gaze direction of the user 105 can be applied to determine a virtual world gaze direction of the user 105 in the virtual environment.

Additionally, a tactile feedback module 181 is configured to provide signals to tactile feedback hardware included in either the HMD 102 or another device operated by the HMD user 105, such as a controller 104. The tactile feedback may take the form of various kinds of tactile sensations, such as vibration feedback, temperature feedback, pressure feedback, etc.

Further, test data collector 118 is configured to monitor and store test data associated with interaction with VR content by the user 105 (e.g., real or simulated). In particular, data may include measurements from physiological sensors 125 located both within HMD 102 and outside of the HMD 102 and from actuator 109, all of which collect information about the physiological state of user 105. Additionally, data may include metadata 117 associated with the generation of VR content, and the interaction of the user 105 with that VR content 115. For example, metadata may include game state data, conditions of the virtual environment, user profiles, view perspectives, change of view perspectives, actions taken by the user 105 (e.g., jump, double jump, move, run, walk, stand, turn, rotate head down or up or around, crawl, free fall, twist, tumble, somersault, etc.), sequence of actions taken by user 105, controller actions, gaze tracking information of user 105, etc.

Figure 1D:
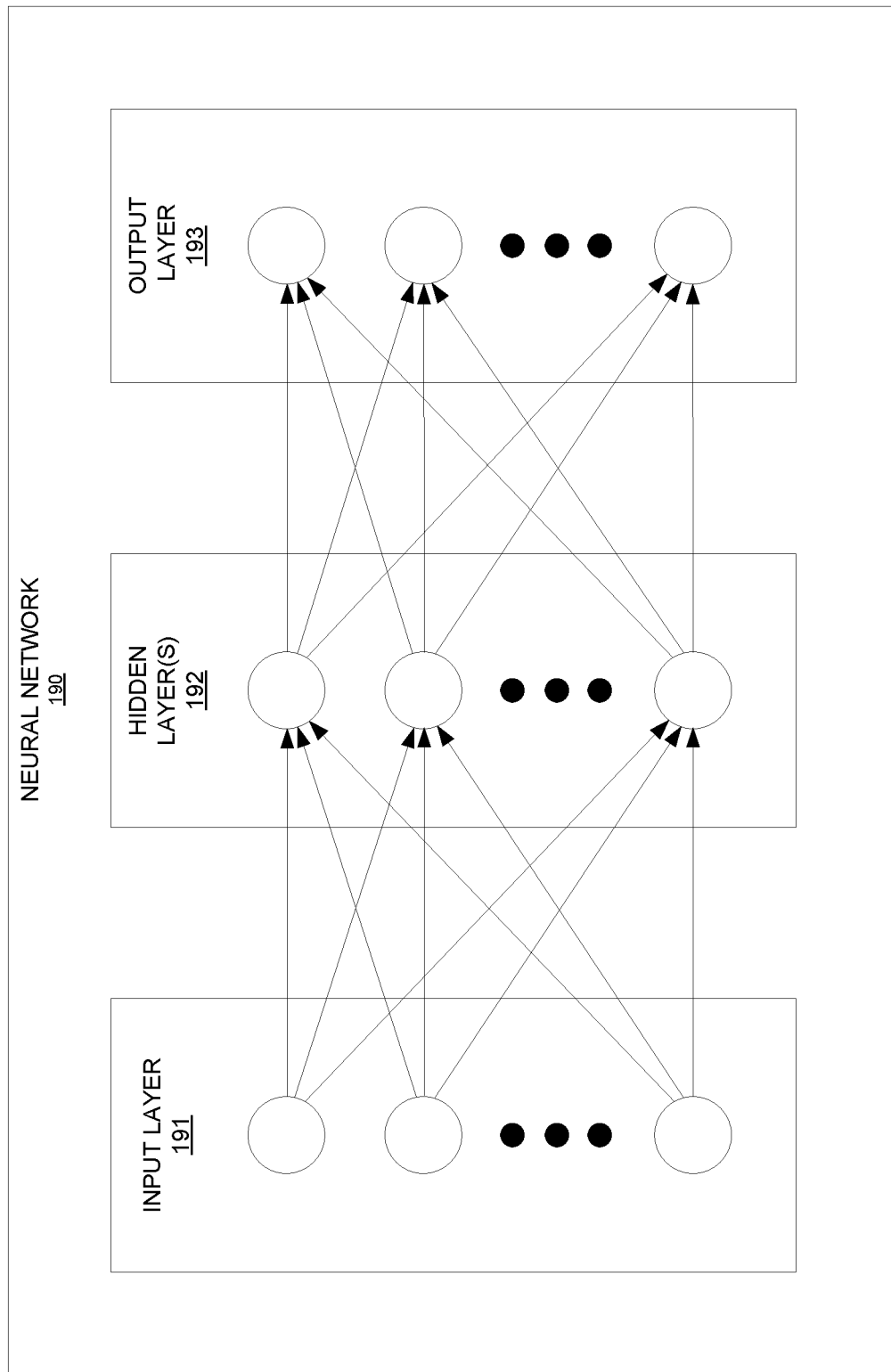
FIG. 1D illustrates an example neural network used to build a discomfort recognition model through training implemented by a deep learning engine, in accordance with one embodiment of the present disclosure.

FIG. 1D illustrates an example neural network used to build a discomfort recognition model through training implemented by the deep learning engine 190 of the discomfort classification modeler 120, in accordance with one embodiment of the present disclosure. In particular, the discomfort classification modeler 120 in system 100A of FIG. 1A is configured to learn what types or patterns of VR content, and/or what actions taken or generated by the user in association with the generation of VR content is likely to induce discomfort and/or sickness in a user (generic, specific, etc.). The discomfort classification modeler 120 may be any computing device, including a back-end server computing device that is coupled to each of the test systems 101a-101n directly or through a network (e.g., local network, internet, etc.).

Specifically, the deep learning engine 190 in the discomfort classification modeler 120 is configured to analyze inputs generated from test users interacting with baseline VR content that has predetermined or true user discomfort and/or sickness responses. As previously described, the inputs include data collected in association with the generation of VR content (e.g., patterns of VR content, and patterns of actions taken or generated by the user in association with the generation of the VR content) and physiological data collected passively by the sensors 125 or actively through the actuator 109. As such, instead of learning why users will react with discomfort and/or sickness when interacting with VR content, the deep learning engine 190 of the discomfort classification modeler 120 is able to recognize which VR content (e.g., types and/or patterns of VR content generated in association with actions taken or generated by the user) when interacted with (e.g., viewing) and/or patterns of actions taken or generated by the user in association with the generation of that VR content will cause a user (e.g., generic user, user of a certain type, etc.) to experience discomfort and/or sickness reactions. These patterns are included within a discomfort model 220. In addition, that recognition allows the discomfort classification modeler 120 to build and/or configure the deep learning engine 190 as a content classification model 121. In addition, the discomfort classification modeler 120 is configured to build and/or configure the deep learning engine 190 as a user classification model 122. The models 220, 121 and 122 are related in that they rely on the same recognition of which VR content when interacted will cause a user to experience discomfort and/or sickness reactions.

As previously introduced, associated VR content data (e.g., patterns of VR content, and/or patterns of actions taken or generated by the user in association with the generation of VR content) and physiological data collected passively by the sensors 125 or actively through the actuator 109 are fed to the deep learning engine 190. The deep learning engine 190 utilizes artificial intelligence, including deep learning algorithms, reinforcement learning, or other artificial intelligence-based algorithms. In that manner, during the learning phase, data is collected from test users that interact with baseline VR content, wherein the baseline VR content is associated with predetermined and expected discomfort and/or sickness reactions. Data is also collected from the VR content engine 111 (e.g., patterns of VR content, metadata, patterns of actions taken or generated by the user in association with the generation of VR content, etc.). The data is used by the deep learning engine 190 to predict discomfort and/or sickness reactions by users given a set of input data. Analysis on the collected data by the deep learning engine 190 may be continually performed to provide updated analytics used for learning which VR content, patterns of VR content, patterns associated with the generation of or interaction with VR content, or patterns associated with simulated or tested user interactions with corresponding VR content, will induce discomfort and/or sickness in users by modifying internal parameters used by the deep learning engine 190. As such, by learning which VR content, patterns associated with the generation of VR content or simulated or tested user interactions, or patterns of VR content induce discomfort and/or sickness in users, the deep learning engine 190 is able to build models that classify VR content, and classify users during a modeling phase.

The neural network 190 represents an example of an automated analysis tool for analyzing data sets to determine which VR content or patterns of VR content will induce discomfort and/or sickness in users. Different types of neural networks 190 are possible. In an example, the neural network 190 supports deep learning that may be implemented by deep learning engine 190. Accordingly, a deep neural network, a convolutional deep neural network, and/or a recurrent neural network using supervised or unsupervised training can be implemented. In another example, the neural network 190 includes a deep learning network that supports reinforcement learning. For instance, the neural network 190 is set up as a Markov decision process (MDP) that supports a reinforcement learning algorithm.

Generally, the neural network 190 represents a network of interconnected nodes, such as an artificial neural network. Each node learns some information from data. Knowledge can be exchanged between the nodes through the interconnections. Input to the neural network 190 activates a set of nodes. In turn, this set of nodes activates other nodes, thereby propagating knowledge about the input. This activation process is repeated across other nodes until an output is provided.

As illustrated, the neural network 190 includes a hierarchy of nodes. At the lowest hierarchy level, an input layer 191 exists. The input layer 191 includes a set of input nodes. For example, each of these input nodes is mapped to VR content data and physiological data collected passively by the sensors 125 or actively through the actuator 109 collected during interactions of test users with VR content (e.g., video game or gaming application, etc.).

At the highest hierarchical level, an output layer 193 exists. The output layer 193 includes a set of output nodes. An output node represents a decision (e.g., prediction) that relates to one or more components of a user game play profiler, for example. As previously described, the output nodes may identify the state of the test user with reference to discomfort and/or sickness. That is, given a set of inputs the output nodes indicate the level of discomfort and/or sickness state a user is predicted to experience as determined by the deep learning engine 190. These results can be compared to predetermined and true discomfort and/or sickness reactions in order to refine and/or modify the parameters used by the deep learning engine 190 to iteratively determine which VR content or patterns of VR content will induce discomfort and/or sickness in users. That is, the nodes in the neural network 190 learn the parameters of the model that can be used to make such decisions when refining the parameters.

In particular, a hidden layer 192 exists between the input layer 191 and the output layer 193. The hidden layer 192 includes "N" number of hidden layers, where "N" is an integer greater than or equal to one. In turn, each of the hidden layers also includes a set of hidden nodes. The input nodes are interconnected to the hidden nodes. Likewise, the hidden nodes are interconnected to the output nodes, such that the input nodes are not directly interconnected to the output nodes. If multiple hidden layers exist, the input nodes are interconnected to the hidden nodes of the lowest hidden layer. In turn, these hidden nodes are interconnected to the hidden nodes of the next hidden layer, and so on and so forth. The hidden nodes of the next highest hidden layer are interconnected to the output nodes. An interconnection connects two nodes. The interconnection has a numerical weight that can be learned, rendering the neural network 190 adaptive to inputs and capable of learning.

Generally, the hidden layer 192 allows knowledge about the input nodes to be shared among all the tasks corresponding to the output nodes. To do so, a transformation $f$ is applied to the input nodes through the hidden layer 192, in one implementation. In an example, the transformation $f$ is non-linear. Different non-linear transformations f are available including, for instance, a rectifier function $f(x)=\max(0,x)$.

The neural network 190 also uses a cost function c to find an optimal solution. The cost function measures the deviation between the prediction that is output by the neural network 190 defined as f(x), for a given input x and the ground truth or target value y (e.g., the expected result). The optimal solution represents a situation where no solution has a cost lower than the cost of the optimal solution. An example of a cost function is the mean squared error between the prediction and the ground truth, for data where such ground truth labels are available. During the learning process, the neural network 190 can use back-propagation algorithms to employ different optimization methods to learn model parameters (e.g., the weights for the interconnections between nodes in the hidden layers 192) that minimize the cost function. An example of such an optimization method is stochastic gradient descent.

In an example, the training dataset for the neural network 190 is from a same data domain. For instance, the neural network 190 is trained for learning which VR content or patterns of VR content will induce discomfort and/or sickness in users. In this illustration, the data domain includes test session data collected for interactions of test users with baseline VR content. In another example, the training dataset is from different data domains. For instance, the neural network 190 is trained for gaming applications, or for a genre of gaming applications.

As such, the neural network 190 may predict or determine which VR content, patterns of VR content, patterns associated with the generation of or interaction with VR content, or patterns associated with simulated or tested user interactions with corresponding VR content, and/or patterns of actions taken or generated by the user in association with the generation of that VR content, induces user discomfort and/or sickness. These patterns identified as inducing discomfort and/or sickness are included within a discomfort model 220. Based on these predictive results, the neural network 190 may also define a predictive model (e.g., content classification model 121) that is used to classify VR content based on the predicted user discomfort and/or sickness. Further, the neural network 190 may also define a predictive model (e.g., user classification model) that is used to classify users based on personalized and predicted determinations of user discomfort and/or sickness when viewing VR content.

Figure 1E:
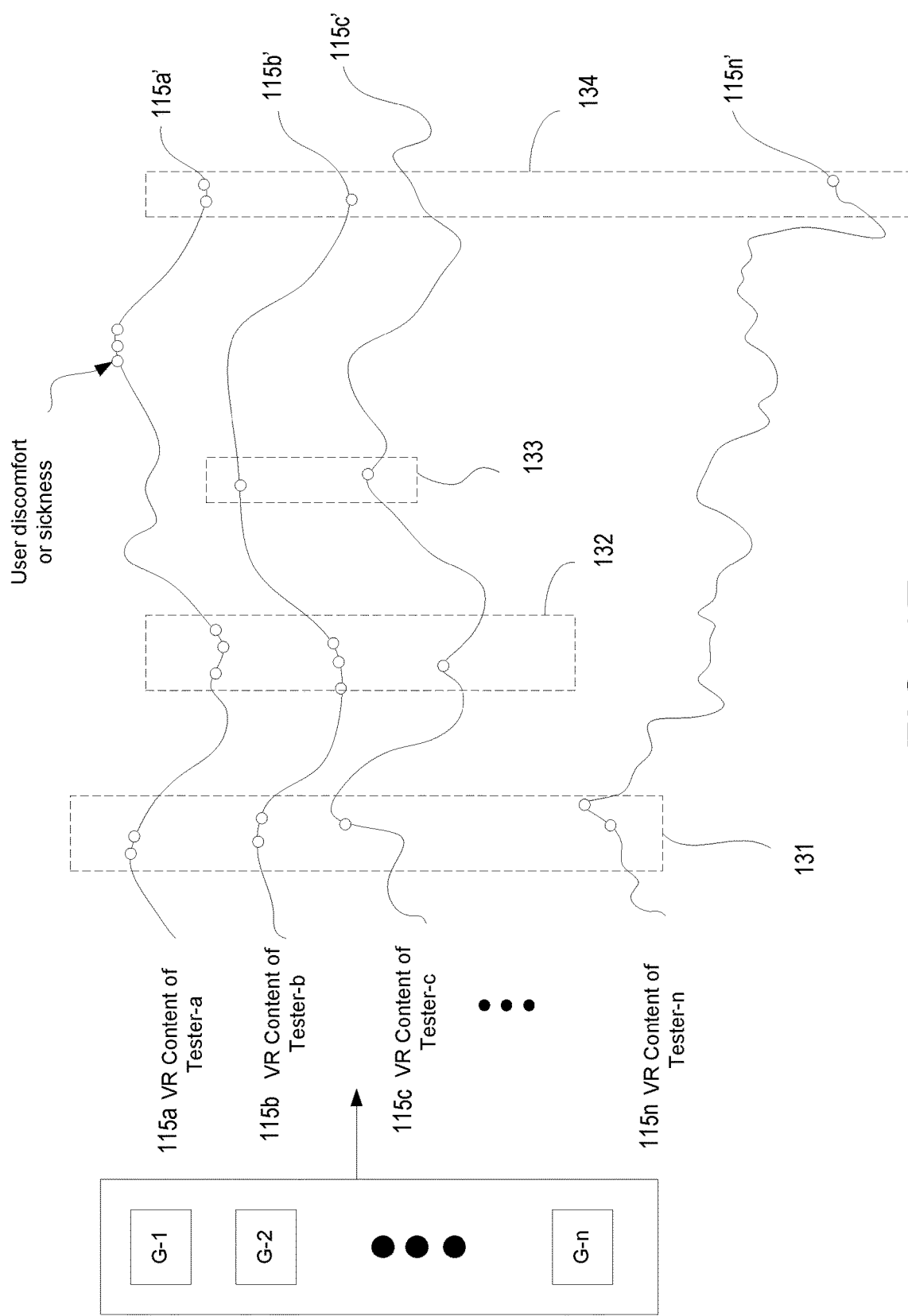
FIG. 1E illustrates the test data that is generated by the system 100A of FIG. 1A, wherein the test data is used for building a discomfort and/or sickness recognition model, in accordance with one embodiment of the present disclosure.

FIG. 1E illustrates the test data that is generated by the system 100A of FIG. 1A, wherein the test data is used for building a discomfort and/or sickness recognition model, in accordance with one embodiment of the present disclosure. As shown, one or more testers (e.g., tester-a through tester-N) interact with one or more test applications (e.g., gaming applications G-1 through G-n). For example, the testers interact with corresponding VR content that is executing on client device 100 using HMD 102. That is, in one embodiment, one application may be used by one or more testers to generate data used for building a discomfort and/or sickness recognition model. In another embodiment, more than one application may be used by one or more testers to generate the data used to build a discomfort and/or sickness recognition model that is configured in part to identify VR content, patterns of VR content, patterns associated with the generation of or interaction with VR content, or patterns associated with simulated or tested user interactions with corresponding VR content, and/or patterns of actions taken or generated by the user in association with the generation of that VR content, that induce discomfort and/or sickness.

As shown, tester-a is interacting with VR content 115*a* shown by line 115*a*' that is generated from a corresponding application, such as gaming application G-1. For illustration purposes only, line 115*a*' is shown as one curved line having peaks and valleys. The path of line 115*a*' may be analogous to the progress through the gaming application G-1. More importantly, at each point along line 115*a*' there is associated portions of VR content 115*a* that is generated and displayed in response to tester-a interaction. Also, at each point, there are associated actions taken or generated by the user in association with the generation of that VR content 115*a*. In particular, specific points identified with an open circle on the curved line showing portions of VR content 115*a* correspond to monitored physiological data (passively or actively collected) indicating discomfort and/or sickness in tester-a during his or her interaction with VR content 115*a*. A snapshot of information may be collected for each point along line 115*a*', including associated VR content, metadata, physiological data, actions taken or generated by the user in association with generation of VR content 115*a*, etc., as previously described. This data may be delivered to the discomfort classification modeler 120 and correlated with other data collected from the other testers to identify or predict patterns of VR content and/or actions taken or generated by the testers in association with generation of or interaction with VR content that induce discomfort and/or sickness.

Similarly, other testers are interacting with other VR content generated by one or more applications G-1 through G-n, and generating data used for identifying or predicting VR content, patterns of VR content, patterns associated with the generation of or interaction with VR content, or patterns associated with simulated or tested user interactions with corresponding VR content, and/or patterns of actions taken or generated by the simulated or test user in association with the generation of that VR content that induce discomfort and/or sickness. For example, tester-b is interacting with VR content 115*b* shown by line 115*b*', tester-c is interacting with VR content 115*c* shown by line 115*c*', . . . and tester-n is interacting with VR content 115*n* shown by line 115*n*'. Data collected in association with each of the VR contents 115*a*-115*n* is delivered to the discomfort classification modeler 120, for example. For purposes of illustration, tester-a, tester-b and tester-c may be interacting with VR content generated from one application, such as G-1. This is shown by the similar shapes to curved lines 115*a*', 115*b*' and 115*c*'. In addition, tester-n is interacting with VR content generated from a separate application, such as G-3.

Whether it is one application used for testing, or multiple applications used for testing, the discomfort classification modeler 120 is able to identify or predict VR content, patterns of VR content, patterns associated with the generation of or interaction with VR content, or patterns associated with simulated or tested user interactions with corresponding VR content, and/or patterns of actions taken or generated by the user in association with the generation of that VR content that reliably induce discomfort and/or sickness in the testers. For example, highlighted box 131 shows identified points in VR content 115*a*, 115*b*, and 115*c* that correlate to tester discomfort and sickness. It happens that these points in box 131 for VR content 115*a*, 115*b*, and 115*c* occur generally at the same progression through the application G-1, as previously introduced. That is, the same patterns of VR content and/or actions taken or generated in association with corresponding VR content are occurring for each of the testers (e.g., tester-a, tester-b, and tester-c). For example, the pattern of VR content may be a FOV having a projected center axis that swings 180 degrees at a high rate, in association with user actions to include running, a double jump, and a quick rotation of head to look down at the landing. Highlighted box 131 includes two points in VR content 115n that is generated through the execution of a separate application G-3, as previously introduced. These two points are associated with a similar pattern of VR content (e.g., FOV having a projected center axis that swings 180 degrees at a high rate) and/or similar patterns of user actions (e.g., running, a double jump, and a quick rotation of head) though they are generated from application G-3 instead of G-1. Discomfort classification modeler 120 is able to make a correlation between the similar VR content, patterns of VR content, patterns associated with the generation of or interaction with VR content, or patterns associated with simulated or tested user interactions with corresponding VR content, and/or patterns of actions taken or generated by the user in association with the generation of that VR content and the induced discomfort and/or sickness in the testers. That is, discomfort classification modeler 120 may identify or predict that the pattern of VR content (FOV having a projected center axis that swings 180 degrees at a high rate) reliably induces discomfort and/or sickness no matter the application source. Also, discomfort classification modeler 120 may identify or predict that the pattern of actions (e g, running, a double jump, and a quick rotation of head) reliably induces discomfort and/or sickness no matter the application source.

Highlighted box 132 shows identified points in VR content 115a, 115b, and 115c that correlate to tester discomfort and sickness. It happens that these points in box 132 for VR content 115a, 115b, and 115c occur generally at the same progression through the application G-1, as previously introduced. That is, the same patterns of VR content and/or actions taken or generated in association with corresponding VR content, for example, are occurring for each of the testers (e.g., tester-a, tester-b, and tester-c). Discomfort classification modeler 120 is able to make a correlation between the similar patterns of VR content and/or patterns actions taken or generated by the testers in association with generation of or interaction of corresponding VR content and the induced discomfort and/or sickness in the testers. As such, a common pattern (e.g., a second pattern) of VR content or actions taken or generated in association with corresponding VR content, or patterns associated with the generation of or interaction with VR content, or patterns associated with simulated or tested user interactions with corresponding VR content, and/or patterns of actions taken or generated by the user in association with the generation of corresponding VR content may be classified as inducing discomfort and/or sickness.

Highlighted box 133 shows identified points in VR content 115b and 115c that correlate to tester discomfort and sickness. These points in box 133 occur generally at the same progression through application G-1, as previously introduced. That is, the same patterns of VR content and/or actions taken or generated in association with corresponding VR content are occurring for each of the testers (e.g., tester-b and tester-c). Though tester-a does not show discomfort in this same area in the progression through application G-1 (e.g., tester-a may be immune to this third associated pattern), discomfort classification modeler 120 may still be able to make a correlation between the similar VR content, patterns of VR content, patterns associated with the generation of or interaction with VR content, or patterns associated with simulated or tested user interactions with corresponding VR content, and/or patterns of actions taken or generated by the user in association with the generation of that VR content and the induced discomfort and/or sickness in the testers. As such, a common pattern (e.g., a third pattern) of VR content or actions taken or generated in association with corresponding VR content may be classified as inducing discomfort and/or sickness by the discomfort classification modeler 120.

Highlighted box 134 shows identified points in VR content 115a, 115b and 115n that correlate to tester discomfort and sickness. These points in box 134 are based on different applications (e.g., G-1 and G-3), but are grouped according to a similar pattern of VR content and/or actions taken or generated by testers in association with generation of or interaction of corresponding VR content. As such, a common pattern (e.g., a fourth pattern) of VR content or patterns associated with the generation of or interaction with VR content, or patterns associated with simulated or tested user interactions with corresponding VR content, and/or patterns of actions taken or generated by the user in association with the generation of that VR content may be classified as inducing discomfort and/or sickness by the discomfort classification modeler 120.

As shown in FIG. 1E, after sufficient test data has been analyzed through a deep learning process, the discomfort classification modeler 120 is able to recognize which VR content, patterns of VR content, patterns associated with the generation of or interaction with VR content, or patterns associated with simulated or tested user interactions with corresponding VR content, and/or patterns of actions taken or generated by the user in association with the generation of that VR content, will induce discomfort and/or sickness. These identified patterns can be included within the discomfort model 220 that can be used to preemptively identify similar patterns in applications under test to understand which applications users may expect to experience discomfort and/or sickness, and also to identify at which points in applications users may expect to experience discomfort and/or sickness.

Figure 1F:
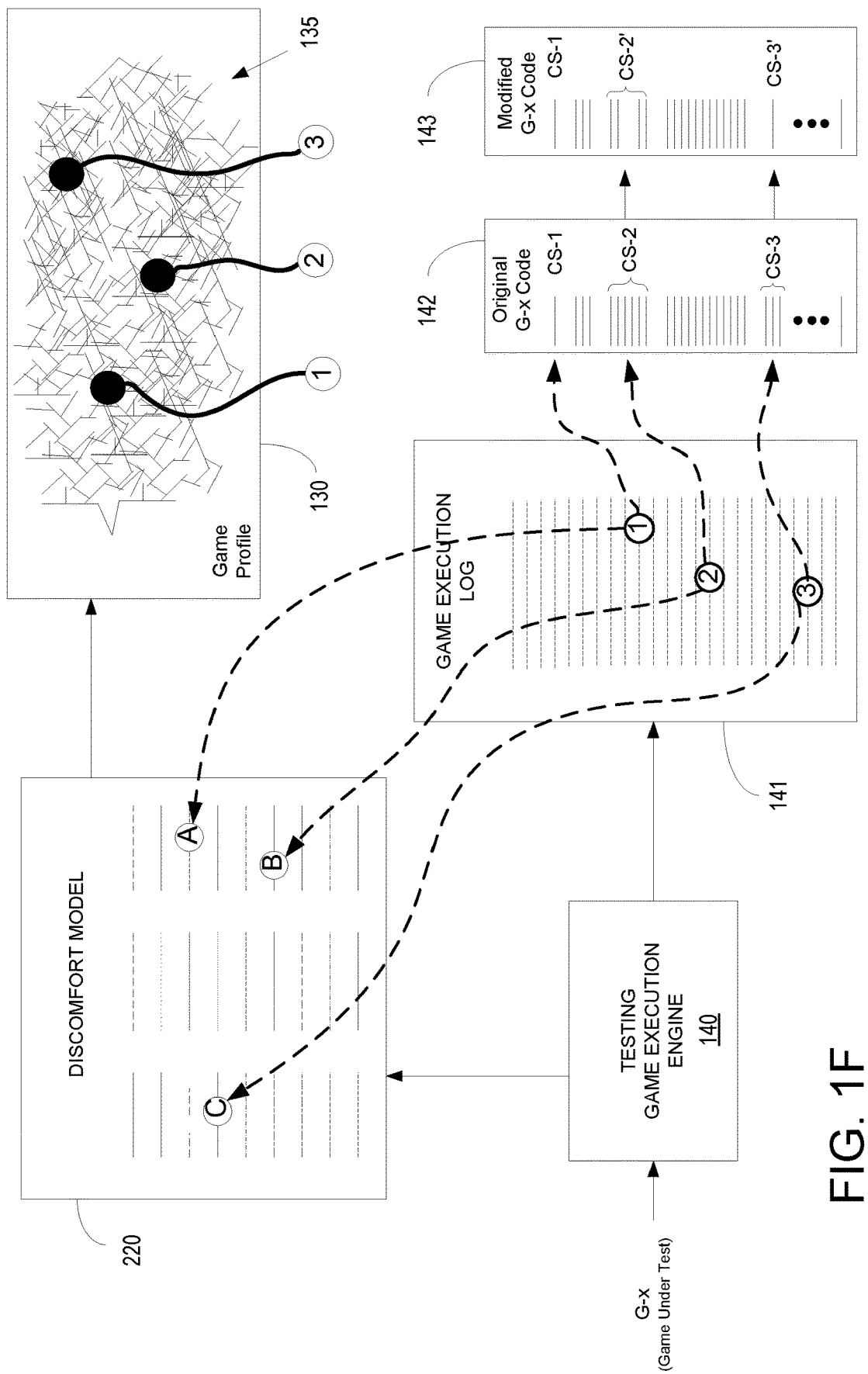
FIG. 1F illustrates the application of a discomfort recognition model to an application under test, wherein the application generates VR content, for purposes of identifying points in the application as executed that are associated with patterns of VR content, and/or patterns of actions taken or generated by the user in association with the generation of that VR content, that induce discomfort and/or sickness, in accordance with one embodiment of the present disclosure.

FIG. 1F illustrates the application of a discomfort model 220 to an application under test (e.g., gaming application, G-x), wherein the application generates VR content, for purposes of identifying points in the application as executed that are associated with VR content, patterns of VR content, patterns associated with the generation of or interaction with VR content, or patterns associated with simulated or tested user interactions with corresponding VR content, and/or patterns of actions taken or generated by the user in association with the generation of that VR content, that induce discomfort and/or sickness, in accordance with one embodiment of the present disclosure. For example, the discomfort model 220 includes one or more items of VR content, patterns of VR content, patterns associated with the generation of or interaction with VR content, or patterns associated with simulated or tested user interactions with corresponding VR content, and/or patterns of actions taken or generated by the user in association with the generation of that VR content that reliably will induce discomfort and/or sickness as determined through testing, as previously described. As shown in FIG. 1E, a plurality of lines is shown, each of which represents a different item of VR content, patterns of VR content, patterns associated with the generation of or interaction with VR content, or patterns associated with simulated or tested user interactions with corresponding VR content, and/or patterns of actions taken or generated by the user in association with the generation of that VR content that is recognized as inducing discomfort and/or sickness in a user.

As shown, the application G-x is executed by the testing game execution engine 140 in order to automatically execute all the various paths and options available in the application. For example, node graph 135 of game profile 130 represents all the various paths that can be taken by a user when interacting with application G-x. The testing game execution engine 140 is able to automatically discover and execute all the paths in node graph 135. In addition, as the testing game execution engine 140 executes application G-x, a game execution log 141 is produced that includes information related to the generation of VR content and how the game was executed, such as controller input, metadata, game state data, etc. Further, the information in log 141 may include or be associated with generated VR content, patterns of VR content, patterns associated with the generation of or interaction with VR content, or patterns associated with simulated or tested user interactions with corresponding VR content, and/or patterns of actions taken or generated by the user in association with the generation of that VR content.

As the application G-x is executed by testing game execution engine 140, data related to the execution, such as the information contained in or related to the information contained in game execution log 141, is compared with information in the discomfort model to identify points in the application G-x that may induce discomfort and/or sickness. This comparison may be performed by processor 205 of FIG. 2A, as further described below. For example, points 1-3 in the game execution log correspond to points in the execution of application G-x that each have been identified as being associated with a corresponding VR content, patterns of VR content, patterns associated with the generation of or interaction with VR content, or patterns associated with simulated or tested user interactions with corresponding VR content, and/or patterns of actions taken or generated by the user in association with the generation of that VR content that will induce discomfort and/or sickness. These points are also identified in the node graph 135. Specifically, point 1 in the execution of application G-x is similar to pattern A in the discomfort mode 220, that identifies a corresponding pattern of VR content and/or patterns of actions taken or generated by the user in association with the generation of that VR content that will induce discomfort and/or sickness. Also point 2 in the execution of application G-x is similar to pattern B in the discomfort mode 220 that identifies a corresponding pattern of VR content and/or patterns of actions taken or generated by the user in association with the generation of that VR content, for example, that will induce discomfort and/or sickness. In addition, point 3 determined from the execution of application G-x is similar to pattern C in the discomfort mode 220 that identifies a corresponding pattern of VR content and/or patterns of actions taken or generated by the user in association with the generation of that VR content, for example, that will induce discomfort and/or sickness. As such, each of the patterns A, B and C are unique, and identify different VR content, patterns of VR content, patterns associated with the generation of or interaction with VR content, or patterns associated with simulated or tested user interactions with corresponding VR content, and/or patterns of actions taken or generated by the user in association with the generation of that VR content that will induce discomfort and/or sickness.

Once these points 1-3 have been identified as being associated with patterns that induce discomfort and/or sickness in users, the corresponding code can also be identified. As shown in FIG. 1F, original G-x code 142 includes sections of code that correspond to various points in the execution of application G-x. For example, point 1 is associated with code section CS-1 in the original G-x code 142, point 2 is associated with code section CS-2, and point 3 is associated with code section CS-3.

After the identification of points 1-3, the developer may make a decision whether to modify the original G-x code 142 in order to reduce potential discomfort and/or sickness. As shown in FIG. 1F, the code CS-1 associated with point 1 is left in its original state. For example, code section CS-1 is represented with one line in the original G-x code 142, and the same line is shown for CS-1 in the modified G-x code 143. However, code CS-2 associated with point 2, and code CS-3 associated with point 3, have been modified to reduce discomfort and/or sickness responses. In particular, code section CS-2, represented by six lines in the original G-x code 142, has been modified to code section CS-2' in the modified G-x code 143 to include four lines (though more than six lines could also show a modification). Similarly, code section CS-3, represented by three lines in the original G-x code 142, has been modified to code section CS-3' in the modified G-x code 143 to include one line.

Figure 2A:
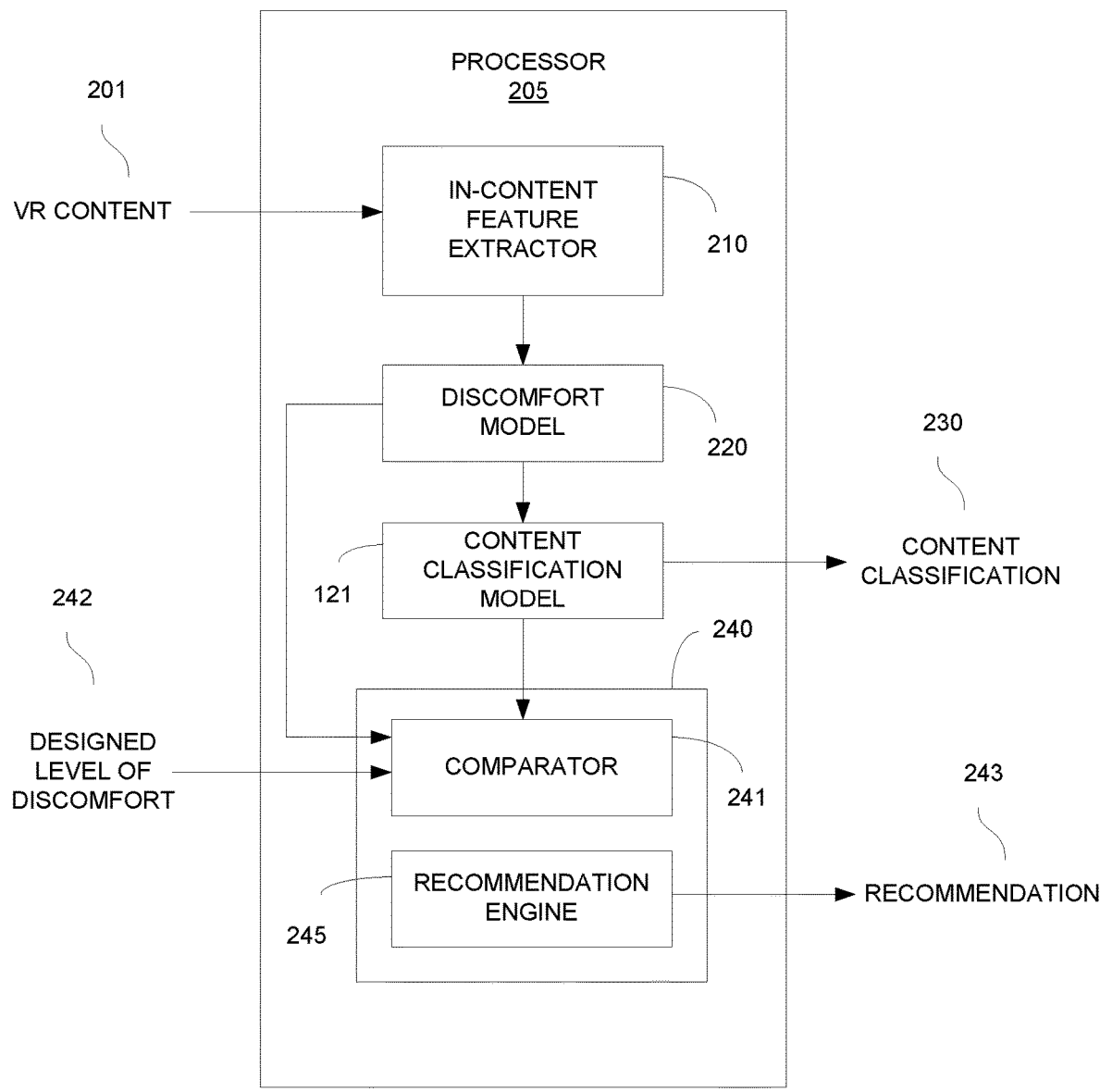
FIG. 2A illustrates a system 200A configured for classifying VR content based on the predicted discomfort and/or sickness of users when viewing VR content as learned by a deep learning engine 190, in accordance with one embodiment of the present disclosure.

FIG. 2A illustrates a system 200A configured for classifying VR content based on the predicted discomfort and/or sickness of users when viewing VR content as learned by a deep learning engine 190, in accordance with one embodiment of the present disclosure. In particular, system 200A utilizes a predictive model (e.g., content classification model 121) as executed by processor 205 that is built by the discomfort classification modeler 120 of FIG. 1A in order to classify VR content in one embodiment.

As shown, VR content 201 is input into the in-content feature extractor 210 to determine characteristics of the VR content 201. For example, VR content may be an application that is executed by the testing game execution engine 140 of FIG. 1F. In addition, this VR content may be any type of content, such as gaming applications, video, simulations, etc. Further, the VR content may be fully developed, or still in its design phase.

In particular, in-content features may define identifiable VR content or patterns of VR content, patterns associated with the generation of or interaction with VR content, or patterns associated with simulated or tested user interactions with corresponding VR content, and/or patterns of actions taken or generated by the user in association with the generation of that VR content that can be used for predicting whether a user may experience discomfort and/or sickness when interacting with that VR content. For example, extractor 210 may randomly select various segments of the VR content, or periodically capture segments of VR content, or identify patterns of actions taken or generated by the user in association with the generation of corresponding VR content. In addition, extractor 210 may specifically search for particular images, scenes, and/or sequence of images or scenes for use as in-content features. For example, extractor 210 may search for scenes or a sequence of scenes that include a horizon. Further, these patterns of VR content, or patterns of actions taken or generated by the user in association with the generation of corresponding VR content, images, scenes and/or sequence of images or scenes may be combined with other VR content (e.g., audio, other sensory input, etc.) as in-content features. In addition, various in-content features may have been previously identified by the content creator (e.g., gaming application developer) that is used for content classification.

The determined in-content features are inputted into the discomfort model 220, which was generated by the discomfort classification modeler 120. That is, the prediction model, or one based on the prediction model, generated by the deep learning engine 190 and used to learn and predict which VR content, patterns of VR content, patterns associated with the generation of or interaction with VR content, or patterns associated with simulated or tested user interactions with corresponding VR content, and/or patterns of actions taken or generated by the user in association with the generation of that VR content, induces user discomfort and/or sickness, is used by system 200A to predict levels of discomfort and/or sickness that may be experienced by a user when interacting with the VR content 201. For example, the discomfort model 220 may predict when a user will experience discomfort and/or sickness, how many times the user will experience discomfort and/or sickness, the degree of discomfort and/or sickness, and the types of discomfort and/or sickness. This information is relevant in determining how a user will react when viewing this particular VR content.

The output from the discomfort model 220 is then delivered to the content classification model 121, previously introduced in FIG. 1A. In particular, based on the predicted discomfort and/or sickness information, the content classification model is configured to identify points in the VR content and/or points in the application associated with the VR content that are likely to induce discomfort and/or sickness in potential users, and based on that information to classify the VR content 210. That is, a content classification 230 for the VR content 201 is generated that follows a predetermined classification system (e.g., high, medium, and low discomfort and sickness levels, etc.). For example, if the discomfort model 220 predicts that numerous instances of discomfort and/or sickness would be experienced by a user (even if the degrees of discomfort corresponding to the instances may be low or mild), then a high discomfort classification 230 may be assigned to VR content 210. The same classification 230 may be given if the VR content 210 is predicted to induce a small number of discomfort and/or sickness reactions by a user, but the degree of discomfort is very severe. On the other hand, if the discomfort model 220 predicts that a limited number of instances of discomfort and/or sickness would be experienced by a user, then a medium discomfort classification 230 may be assigned to VR content 210. The same classification 230 may be given if the VR content 210 is predicted to induce a large number of discomfort and/or sickness reactions by a user, but the degree of discomfort is at a middle level between high and low. Also, if the discomfort model 220 predicts that zero or a negligible number of instances of discomfort and/or sickness would be experienced by a user, then a low discomfort classification 230 may be assigned to VR content 210. The same classification 230 may be given if the VR content 210 is predicted to induce a large number of discomfort and/or sickness reactions by a user, but the degree of discomfort is very low.

Though a classification system is described as having three levels (e.g., low, medium, and high), it is understood that embodiments of the present invention can accommodate different types of classification systems that can provide notification as to whether or not a user will experience discomfort and/or sickness when viewing a particular item of VR content, and the levels or degrees of discomfort and/or sickness experienced. As such, there may be less than or more than three levels indicating discomfort and/or sickness defined using different criteria.

In one embodiment, the content classification 230 is used by potential users that want to interact with VR content 201. For example, if the classification 230 indicates that a high level of discomfort and/or sickness may be expected (e.g., a large amount or a high degree of discomfort and/or sickness), a user that does not want to potentially experience that discomfort will choose not to interact with VR content 201. The same may be true to a user that previously had a bad discomfort and/or sickness reaction when interacting with another VR content that had the same content classification 230 (e.g., high). On the other hand, a user that embraces or is unaffected by that type of discomfort and/or sickness may actively seek out VR content 201 that is classified as inducing high levels of discomfort and/or sickness. For instance, that user may not experience any discomfort and/or sickness with content having the same classification 230, or even may enjoy that discomfort and/or sickness.

In another embodiment, the content classification 230 is used by developers during the design phase to identify faults within the VR content 201 or a segment of VR content 201, or to make sure that the VR content 201 is of the correct level. For example, the information outputted from the discomfort model 220 (e.g., degree or level of discomfort reactions, number of discomfort reactions, etc.) may be compared with a targeted level of discomfort for the VR content 201 (wherein the VR content is designed to produce the targeted level of discomfort) by the comparator 241 of the fault indicator 240 to determine if there is a match or mismatch. If there is a mismatch, the VR content may be faulty. For example, if the VR content 201 is intended to not induce any discomfort and/or sickness, but the discomfort model 220 predicts that discomfort and/or sickness is induced, this may indicate a problem with the coding of the VR content 201 (e.g., the right and left images that give stereoscopic impressions may be misaligned). For example, recommendation engine 245 may provide a notification/recommendation 243 of the mismatch, and may further identify the type of mismatch, or reason for the mismatch. A developer knowing there is a mismatch may then go back and fix the problem.

If there is a match as determined by the comparator 241, then the developer is on track in developing the VR content 201. The recommendation engine 245 may provide a notification/recommendation 243 of the match. For example, the VR content 201 may be targeted to a specific type of user that is aligned with a particular classification of VR content. For instance, those users may enjoy or desire high levels of discomfort and/or sickness when interacting with VR content. In that case, the developer may be designing VR content 201 to induce high levels of discomfort and/or sickness. In that case, the developer may input VR content 201 or a segment of VR content 201 into system 200A to predict the level of discomfort and/or sickness induced in a user interacting with VR content 201. That information is compared against the designed level of discomfort 242 by the comparator 241 to make sure that the predicted level of discomfort will eventually match the designed level of discomfort. While the present embodiment uses discomfort and levels of discomfort, the same result may be obtained using predicated and designed content classifications because the content classification is based on the predicted levels of discomfort.

Figure 2B:
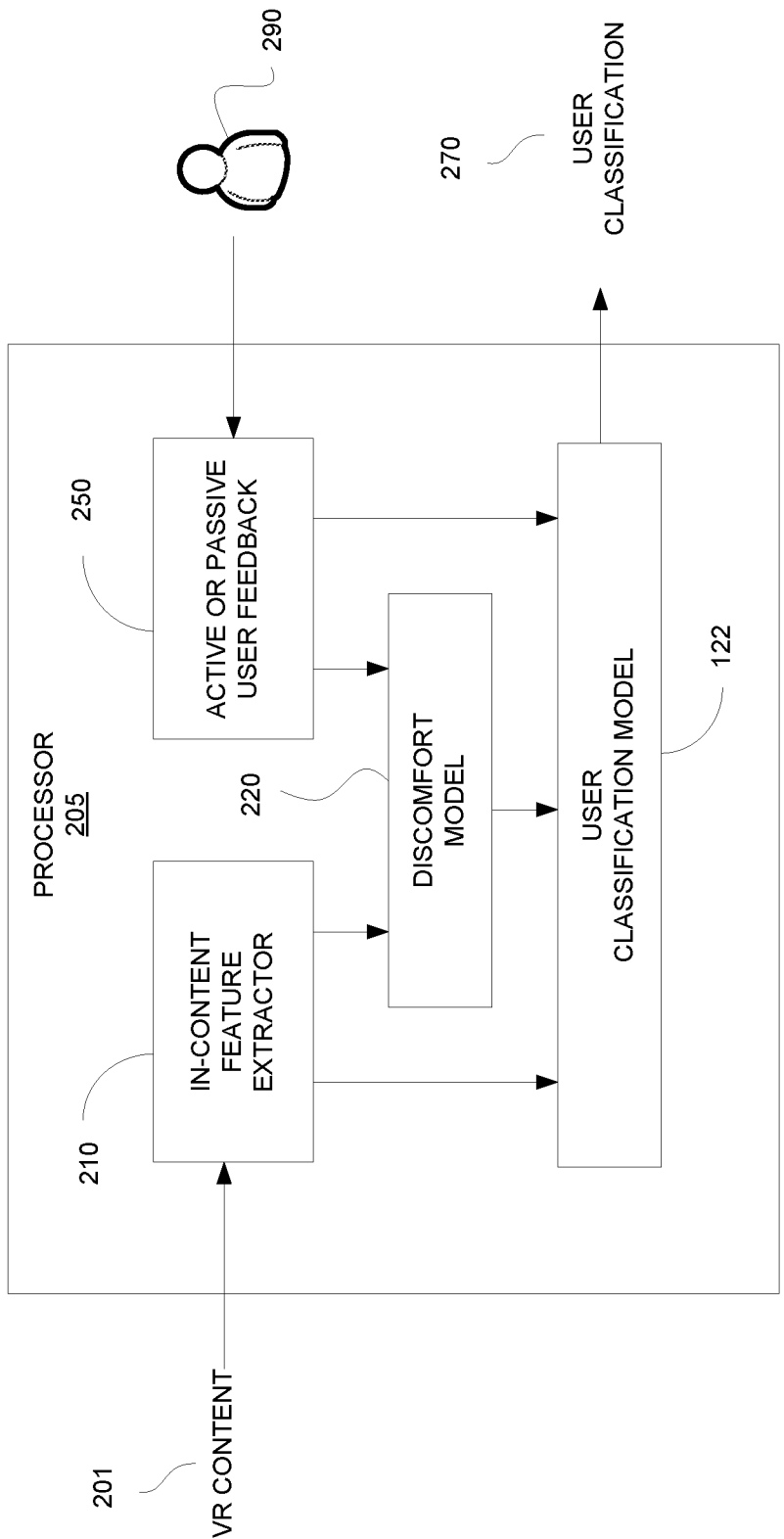
FIG. 2B illustrates a system configured for classifying a user based on tested levels of discomfort that are aligned with predicted levels of discomfort determined by a discomfort recognition model that is built by a deep learning engine, in accordance with one embodiment of the present disclosure.

FIG. 2B illustrates a system 200B configured for classifying a user 290 based on tested levels of discomfort that are aligned with predicted levels of discomfort determined by a discomfort recognition model that is built by a deep learning engine 190 of the discomfort classification modeler 120, in accordance with one embodiment of the present disclosure.

As shown, VR content 201 is input into the in-content feature extractor 210 to determine characteristics of the VR content 201, as previously described in relation to FIG. 2A. For example, VR content 201 may be an application that is executed by the testing game execution engine 140 of FIG. 1F. For example, in-content features may define identifiable VR content, patterns of VR content, patterns associated with the generation of or interaction with VR content, or patterns associated with simulated or tested user interactions with corresponding VR content, and/or patterns of actions taken or generated by the user in association with the generation of that VR content that can be used for predicting whether a user may experience discomfort and/or sickness during interaction with that VR content, and also may be compared against test data to classify user 290. In one embodiment, the VR content 201 includes baseline VR content 201 that is known to induce specific levels or types of discomfort and/or sickness in test users (e.g., test user 105). For example, a typical, test user 105 will react in a specific way to the baseline VR content. Reactions of user 290 may be compared to predicted reactions of the typical, test user 105 to classify user 290 based on tested discomfort and/or sickness reactions.

In addition, active or passive feedback 250 is also collected from user 290. For example, physiological data associated with user 290 may be collected while user 290 is interacting with VR content 201, as previously described. The physiological data may be passively monitored (e.g., using sensors 125), or actively monitored (e.g., actively querying user 290, or having user 290 input data).

The extracted in-content features of VR content 201 are input into discomfort model 220, which was generated by the discomfort classification modeler 120. As such, the discomfort model 220 will determine and output a predicated level of discomfort and/or sickness that may be experienced by a user when interacting with the VR content 201.

The output from the discomfort model 220 is then delivered to the user classification model 122, previously introduced in FIG. 1A. In one embodiment, the predicted discomfort and/or sickness is compared with the active or passive user feedback 250 from user 290 to determine a classification for user 290. That is, reactions of user 290 may be compared to predicted reactions of the typical, test user 105 to classify user 290 based on tested discomfort and/or sickness reactions. In particular, based on the predicted discomfort and/or sickness information, as well as tested discomfort and/or sickness information obtained from user 290, the user classification model is configured to classify user 290 giving an indication how user 290 is affected by VR content. Content classification 270 may follow a predetermined classification system (e.g., high influence, medium influence, and low influence, etc.). For example, if VR content 201 or a pattern of VR content 201 is predicted to induce high levels of discomfort and may be classified as a high discomfort inducing content, but user 290 does not react in the same manner (e.g., experiences no or limited discomfort), then the user classification model 122 may classify user 290 at a low level of classification 270 indicating that user 290 is not greatly affected by VR content that is known to induce discomfort in typical, test users 105. On the other hand, if the discomfort model 220 predicts a high level of discomfort experienced by test users 105, and user 290 also experiences high level of discomfort, then both sets of data are aligned, and user 290 may be classified at a high level indicating that user 290 is highly influenced by high discomfort inducing VR content.

In still another embodiment, the user classification model 122 directly receives as input the in-content features and the active or passive user feedback 250 to classify user 290. That is, the deep learning engine 190 has learned to analyze reactions by various types of test users and classify those users based on their corresponding reactions. The classification is aligned with the VR content classification model 121, in one embodiment. For example, VR content 201 that consistently induces high discomfort in user 290 indicates that user 290 is highly susceptible to high discomfort inducing VR content, and may be accordingly classified at a high level. Continued alignment may indicate that user 290 is susceptible to discomfort VR content, and is accordingly classified at a medium level, or that user 290 is not susceptible to discomfort VR content is accordingly classified at a low level.

Figure 3:
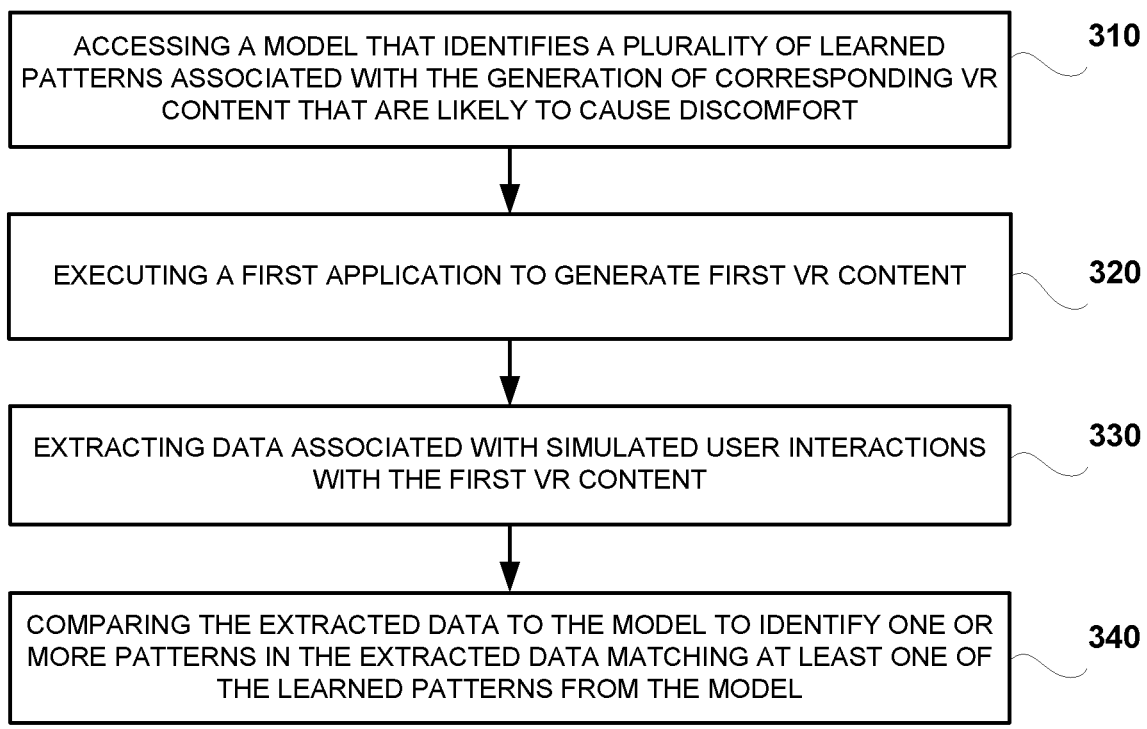
FIG. 3 is a method for classifying VR content based on the modeled level of discomfort determined by a discomfort recognition model that is built by a deep learning engine, in accordance with one embodiment of the present disclosure.

With the detailed description of the various modules of the VR content classification system, a method for classifying VR content based on predicted levels of discomfort and/or sickness inducted by that VR content is now described in relation to flow diagram 300 of FIG. 3, in accordance with one embodiment of the present disclosure. The method outlined in flow diagram 300 is implemented by the systems and/or components of FIGS. 1A-1F and 2A-2B in embodiments.

The method begins at operation 310, and includes accessing a model that identifies a plurality of learned patterns associated with the generation of corresponding VR content that are likely to cause discomfort. The generated model also predicts a level of discomfort experienced by a participating user when interacting with corresponding virtual reality (VR) content. For example, content classification model 121 may be generated at operation 310, and is based on the discomfort model 220 generated by modeler 120 that has learned to recognize which VR content (e.g., types and/or patterns of VR content) when interacted with (e.g., viewing), or patterns of VR content, patterns associated with the generation of or interaction with VR content, or patterns associated with simulated or tested user interactions with corresponding VR content, and/or patterns of actions taken or generated by the user in association with the generation of that VR content will cause to user 105 to experience discomfort and/or sickness reactions.

In particular, when building the model, a deep learning engine may be configured to receive physiological data from test users during their interactions with baseline VR content, as previously described. The deep learning engine analyzes baseline VR content data and physiological data collected passively or actively from test users to learn which VR content (e.g., types, patterns, etc.) when interacted with will cause a user to experience discomfort and/or sickness reactions. As such, over time, input data related to VR content and physiological reactions to VR baseline content can be aligned with known and expected reactions to the VR baseline content. In that manner, certain VR content, patterns of VR content, patterns associated with the generation of or interaction with VR content, or patterns associated with simulated or tested user interactions with corresponding VR content, and/or patterns of actions taken or generated by the user in association with the generation of that VR content may be recognized as inducing discomfort and/or sickness in test users, and applied to classify VR content or users based on predicted discomfort and/or sickness induced or experienced by users.

At operation 320, the method includes executing a first application to generate first VR content. For example, the first application is executed by the testing game execution engine 140 of FIG. 1F to simulate user interaction with all the various paths available in the first application.

At operation 330, the method includes extracting data associated with simulated user interactions with the first VR content generated during execution of the first application. This data is applied to the model. The extracted data includes characteristics of the first VR content generated during the simulation of user interaction with the first VR content. The data may include VR content, patterns of VR content, patterns associated with the generation of or interaction with VR content, or patterns associated with simulated or tested user interactions with corresponding VR content, and/or patterns of actions taken or generated by the user in association with the generation of that VR content. Further, the data may include other in-content features including executable code, at least one static image, a sequence of static images, video, audio, etc. For example, various segments of the VR content may be randomly selected, or segments at periodic intervals may be selected. In addition, particular types of images, scenes, and/or sequence of images or scenes may be identified and used as in-content features. This data is used to classify the first VR content in terms of identifying points in the first VR content or first application that are likely to cause discomfort and/or sickness.

At operation 340, the method includes comparing the extracted data to the model to identify one or more patterns in the extracted data matching at least one of the learned patterns from the model such that the one or more patterns are likely to cause discomfort. For example, VR content, patterns of VR content, patterns associated with the generation of or interaction with VR content, or patterns associated with simulated or tested user interactions with corresponding VR content, and/or patterns of actions taken or generated by the user in association with the generation of that VR content that match the learned patterns can also be determined to likely cause discomfort and/or sickness. The first content may be further classified by identifying points in the first application (e.g., code) that are associated with the matched patterns. Once the first application is classified, further actions may be performed, such as determining a level of discomfort for a prospective user of the first application, and providing notification of the level of discomfort to the prospective user.

Further, the method includes determining a level of discomfort based on the first VR content, or more specifically, based on the in-content features and/or extracted data of the first VR content. That is, the model can be configured to predict what types and levels of discomfort and/or sickness will be induced by an interacting user. For example, the model may predict when a user will experience discomfort and/or sickness, how many times the user will experience discomfort and/or sickness, the degree of discomfort and/or sickness, and the types of dismount and/or sickness.

The method includes assigning a discomfort classification for the first VR content based on the predicted and determined level of discomfort. For example, the classification may follow a predetermined classification system (e.g., high, medium, and low discomfort and/or sickness levels, etc.), as previously described. For example, if the model predicts that the first VR content will induce high levels of discomfort (e.g., number, frequency, degree, etc.) in a user, then the first VR content may be classified at a high discomfort classification. Also, if the model predicts that the first VR content will induce medium levels of discomfort in a user, then the first VR content may be classified at a medium discomfort classification. Further, if the model predicts that the first VR content will induce low levels of discomfort in a user, then the first VR content may be classified at a low discomfort classification. It is important to note that the predetermined classification system may accommodate different types of classification, wherein each system can provide notification as to whether or not a user will experience discomfort and/or sickness when viewing a particular item of VR content, and the levels or degrees of discomfort and/or sickness experienced in embodiments. That is, there may be less than or more than three levels of indicating discomfort and/or sickness.

The classification of the first VR content may be further used as notification. For example, the discomfort classification may provide notification to a prospective user as to the type of content included in the first VR content. That is, the discomfort classification of the first VR content may inform the user the degree of discomfort to be expected during interaction. If the experience of the prospective user closely follows the discomfort classification, then the user may avoid VR content that has a high discomfort classification (unless the user is actively seeking out that type of content), and seek out VR content with lower classifications. Also, if the experience of the prospective user does not follow the discomfort classification, then the user may find that VR content with a high discomfort classification has no effect on the user and may seek out or at least include for consideration VR content with the high discomfort classification.

The classification of the first VR content may be further used by developers during a design or development phase to ensure that the first VR content is developed according to specifications. For example, the first VR content may be designed to meet a certain or targeted level of discomfort and/or sickness as predicted by the model generated at 310. In one case, the first VR content may be targeted to specific users, such as those users who want high levels or numbers of discomfort and/or sickness reactions. As such, the determined level of discomfort and/or sickness as predicted by the model is compared against a targeted level of discomfort designed for the first VR content. Notification of a mismatch is provided when the predicated level of discomfort does not match the targeted level of discomfort. Further, a recommendation may be provided when there is a mismatch. For instance, the recommendation may point out that specific code is faulty, or that specific instances of VR content need to be changed to induce the proper or targeted discomfort and/or sickness reactions in a user.

In still another embodiment, the method outlined in flow diagram 300 may be modified once the model that predicts discomfort levels for corresponding VR content is known. In that manner, the method includes applying a plurality of first in-content features derived from a first VR content to the model that predicts a level of discomfort experienced by a user when interacting with corresponding content. The method includes determining a level of discomfort based on the first VR content. The method further includes assigning a discomfort classification for the first VR content based on the predicted and/or determined level of discomfort.

Figure 4:
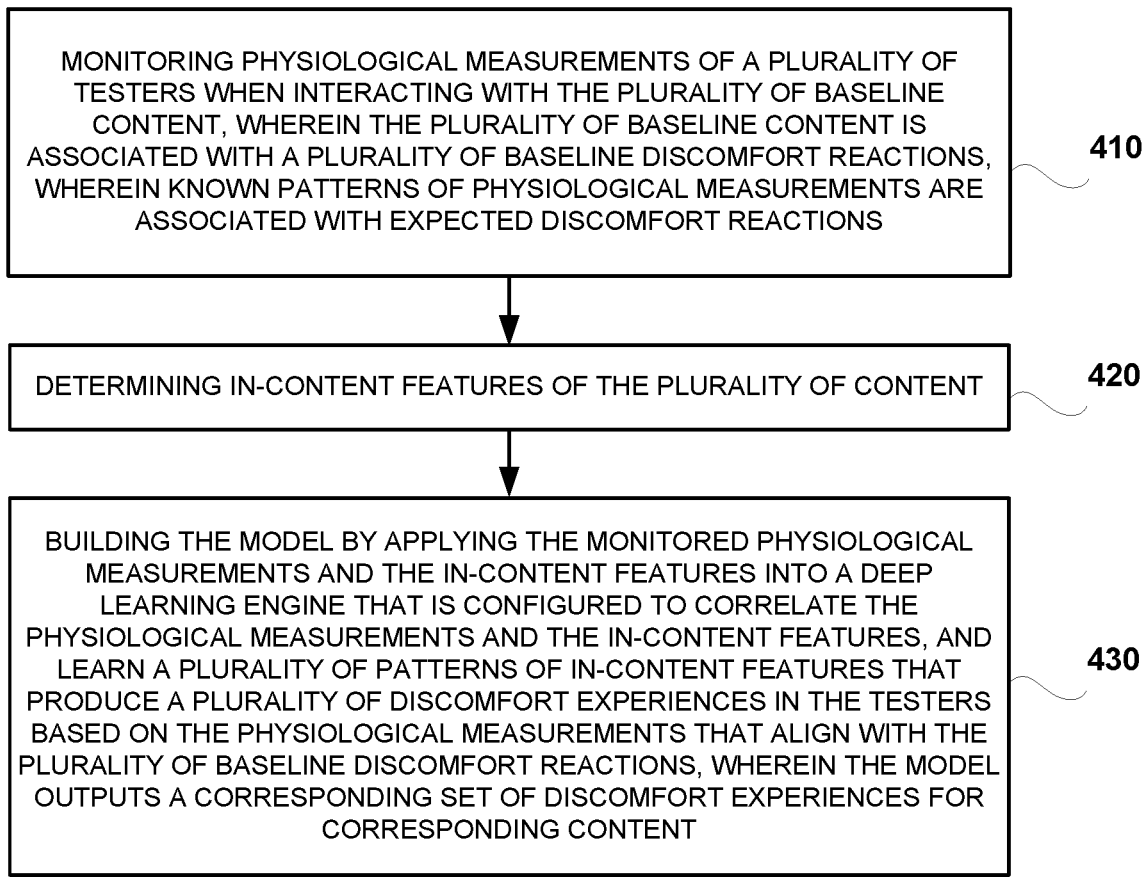
FIG. 4 is a method for building or training a discomfort recognition model by a deep learning engine, wherein the model is configured for determining and/or correlating discomfort by a user when interacting with VR content or patterns of VR content, in accordance with one embodiment of the present disclosure.

FIG. 4 is a flow diagram 400 illustrating a method for building or training a discomfort recognition model by a deep learning engine, wherein the model is configured for determining and/or correlating discomfort by a user when interacting with VR content or patterns of VR content, in accordance with one embodiment of the present disclosure. For example, the method outlined in flow diagram 400 may be implemented by the deep learning engine 190 of the discomfort classification modeler 120 to learn under what conditions a user will experience discomfort and/or sickness when viewing VR content. Specifically, the method outlined in flow diagram 400 may be implemented to recognize which VR content (e.g., types, patterns, etc.) when interacted with will cause a user to experience discomfort and/or sickness reactions. The method outlined in flow diagram 400 is implemented by the systems and/or components of FIGS. 1A-1F and 2A-2B in embodiments.

The method outlined in flow diagram 400 is implemented in a testing environment in which a plurality of test users is monitored while interacting with a plurality of baseline VR content. That is, a plurality of testing applications is executed for interaction by the plurality of testers to generate the plurality of baseline content. In particular, at operation 410, the method includes monitoring physiological measurements of a plurality of testers when interacting with a plurality of baseline content. The baseline content is associated with a plurality of baseline discomfort reactions that are considered to be true. That is, physiological measurements of the plurality of testers are monitored when the testers are interacting with the plurality of baseline VR content, wherein the plurality of baseline VR content is associated with a plurality of baseline discomfort reactions, wherein known patterns of physiological measurements are associated with expected discomfort reactions.

Physiological measurements may be passively monitored. For example, physiological data may include electrogastrography, galvanic skin resistance, brain activity, heart rates, eye movement, head movement, etc. These measurements may be correlated with in-content features, as will be described below. In addition, known patterns of physiological measurements are associated with expected discomfort reactions. For example, a correlation may be made between increased galvanic skin resistance (e.g., indicating more sweating) and increased discomfort. Though a direct correlation may not be proven between any one measurement, the method of flow diagram 400 is able to learn and/or recognize which VR content (e.g., types, patterns, combinations of patterns, etc.) when interacted with will cause a user to experience discomfort and/or sickness reactions. For example, patterns of VR content and/or patterns of actions taken or generated by the user in association with the generation of corresponding VR content may be identified as causing a user to experience discomfort and/or sickness reactions.

At 420, the method includes extracting data associated with tester interactions with the baseline VR content generated during execution of the plurality of testing applications. As previously described, the data includes VR content, patterns of VR content, patterns associated with the generation of or interaction with VR content, or patterns associated with simulated or tested user interactions with corresponding VR content, and/or patterns of actions taken or generated by the user in association with the generation of that VR content, that is then used to predict whether a user may experience discomfort and/or sickness when interacting with that VR content. For example, this content may include random images or sequence of images, periodic images or sequence of images, specific images or sequence of images with specific content or objects (e.g., horizon, etc.), or predefined images or sequence of images (e.g., delivered by developer), or patterns of VR content, and/or patterns of actions taken or generated by the user in association with the generation of corresponding VR content.

At 430, the method includes building the model by applying the monitored physiological measurements and the extracted data into a deep learning engine. The deep learning engine is configured to correlate the physiological measurements with the data associated with tester interactions to determine a plurality of patterns of learned patterns that are likely to produce discomfort experiences in the testers based on the physiological measurements that align with the plurality of baseline discomfort reactions. That is, the physiological measurements obtained during testing are input into the deep learning engine to obtain predicted outputs of discomfort reactions, wherein the predicted outputs are compared against true or known outputs in order to modify parameters in the deep learning engine so that over time, the predicted outputs closely align with the true or known outputs.

Figure 5:
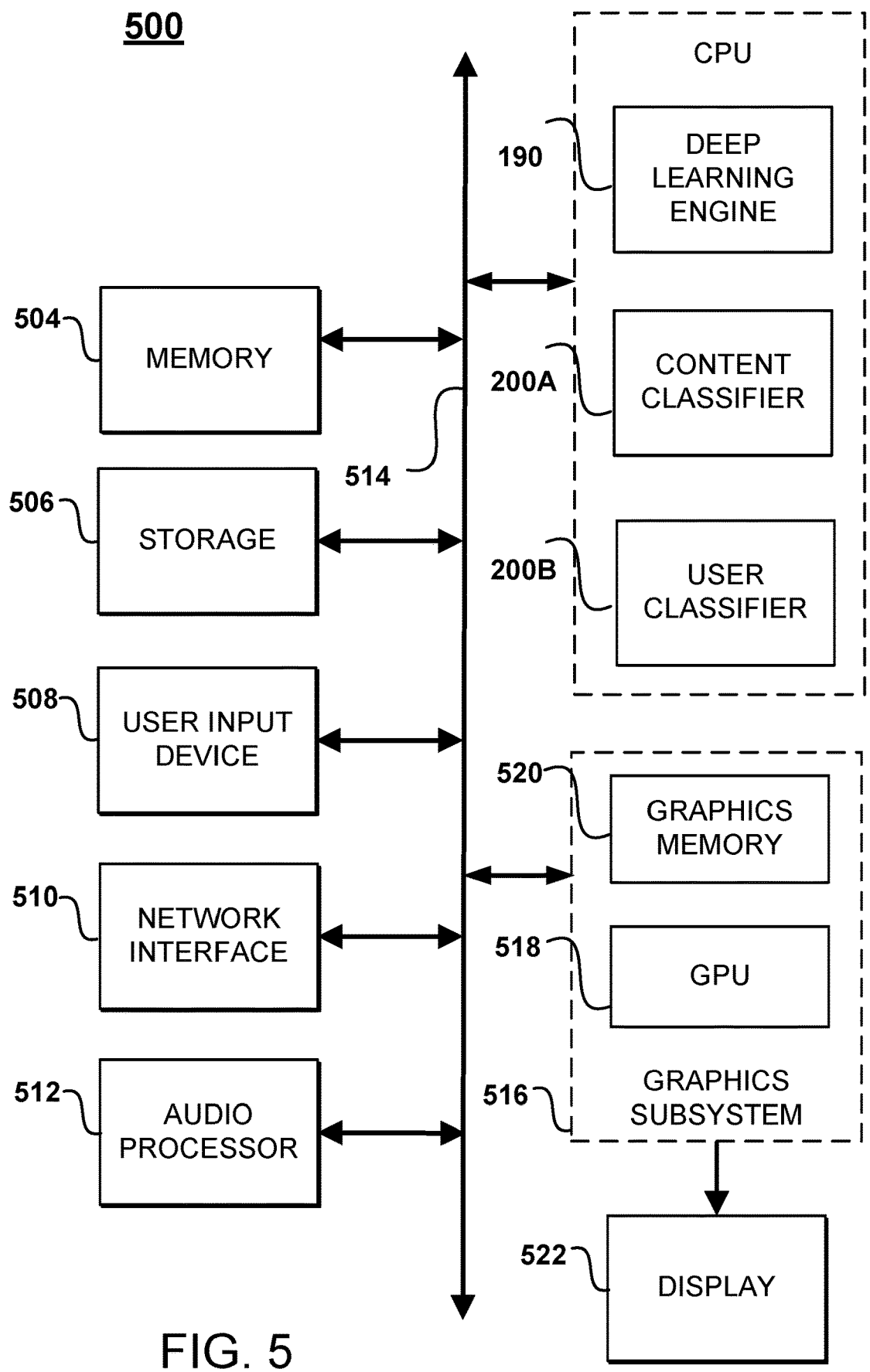
FIG. 5 illustrates components of an example device that can be used to perform aspects of the various embodiments of the present disclosure.

In another embodiment, the physiological data may be actively monitored. That is, the plurality of testers is monitored when interacting with the baseline content. In particular, the method includes monitoring for a plurality of tester responses that indicate a plurality of discomfort reactions when interacting with the baseline VR content. That is, the tester responses are actively monitored, such as when a user activates an actuator (e.g., button) indicating when the user is experiencing discomfort and/or sickness. These responses may be correlated with in-content features, as described below. In the active case, the model is built by the deep learning engine by applying the plurality of tester responses and the in-content features into a deep learning engine that is configured to correlate the plurality of tester responses and the in-content features and/or extracted data associated with the generation of corresponding VR content. In that manner, the deep learning engine is configured to learn a plurality of patterns of in-content features that produce a plurality of discomfort experiences in the testers that align with the plurality of baseline discomfort reactions, wherein the model may output a corresponding set of discomfort experiences for corresponding content FIG. 5 illustrates components of an example device that can be used to perform aspects of the various embodiments of the present disclosure. For example, FIG. 5 illustrates an exemplary hardware system suitable for implementing a device in accordance with one embodiment. This block diagram illustrates a computer system 500, such as a personal computer, video game console, personal digital assistant, or other digital device, suitable for practicing an embodiment of the invention. Computer system 500 includes a central processing unit (CPU) 502 for running software applications and optionally an operating system. CPU 502 may be comprised of one or more homogeneous or heterogeneous processing cores.

In accordance with various embodiments, CPU 502 is one or more general-purpose microprocessors having one or more processing cores. Further embodiments can be implemented using one or more CPUs with microprocessor architectures specifically adapted for highly parallel and computationally intensive applications, such as media and interactive entertainment applications, of applications configured for deep learning, content classification, and user classifications. For example, CPU 502 may be configured to include deep learning engine 190 that is configured to recognize which VR content (e.g., types and/or patterns of VR content) when interacted with will cause a user to experience discomfort and/or sickness reactions. In addition, the CPU 502 may be configured to include the content classifier 200A, in which the recognition of which VR content induces discomfort and/or sickness reactions in users can be utilized to classify content according to corresponding predicted levels of discomfort and/or sickness induced by that content. Further, CPU 502 may be configured to include the user classifier 200B, in which the recognition of which VR content induces discomfort and/or sickness reactions in users can be utilized to classify users according to tested levels of discomfort and sickness reactions when those users are interacting with VR content.

Memory 504 stores applications and data for use by the CPU 502. Storage 506 provides non-volatile storage and other computer readable media for applications and data and may include fixed disk drives, removable disk drives, flash memory devices, and CD-ROM, DVD-ROM, Blu-ray, HD-DVD, or other optical storage devices, as well as signal transmission and storage media. User input devices 508 communicate user inputs from one or more users to the computer system 500, examples of which may include keyboards, mice, joysticks, touch pads, touch screens, still or video cameras, and/or microphones. Network interface 510 allows computer system 500 to communicate with other computer systems via an electronic communications network, and may include wired or wireless communication over local area networks and wide area networks such as the Internet. An audio processor 512 is adapted to generate analog or digital audio output from instructions and/or data provided by the CPU 502, memory 504, and/or storage 506. The components of computer system 500, including CPU 502, memory 504, data storage 506, user input devices 508, network interface 510, and audio processor 512 are connected via one or more data buses 522

A graphics subsystem 514 is further connected with data bus 522 and the components of the computer system 500. The graphics subsystem 514 includes a graphics processing unit (GPU) 516 and graphics memory 518. Graphics memory 518 includes a display memory (e.g., a frame buffer) used for storing pixel data for each pixel of an output image. Graphics memory 518 can be integrated in the same device as GPU 516, connected as a separate device with GPU 516, and/or implemented within memory 504. Pixel data can be provided to graphics memory 518 directly from the CPU 502. Alternatively, CPU 502 provides the GPU 516 with data and/or instructions defining the desired output images, from which the GPU 516 generates the pixel data of one or more output images. The data and/or instructions defining the desired output images can be stored in memory 504 and/or graphics memory 518. In an embodiment, the GPU 516 includes 3D rendering capabilities for generating pixel data for output images from instructions and data defining the geometry, lighting, shading, texturing, motion, and/or camera parameters for a scene. The GPU 516 can further include one or more programmable execution units capable of executing shader programs. In one embodiment, GPU 516 may be implemented within deep learning engine 190 to provide processing power, such as for the deep learning engine 190.

The graphics subsystem 514 periodically outputs pixel data for an image from graphics memory 518 to be displayed on display device 520. Display device 520 can be any device capable of displaying visual information in response to a signal from the computer system 500, including CRT, LCD, plasma, and OLED displays. Computer system 500 can provide the display device 520 with an analog or digital signal.

It should be understood that the embodiments described herein may be executed on any type of client device. In some embodiments, the client device is a head mounted display (HMD). For example, the HMD may be used during testing of users to learn which VR content or patterns of VR content induces discomfort and/or sickness. Further, the HMD may be used to classify or calibrate a user according to tested discomfort and/or sickness responses to VR content (e.g., baseline VR content).

Figure 6:
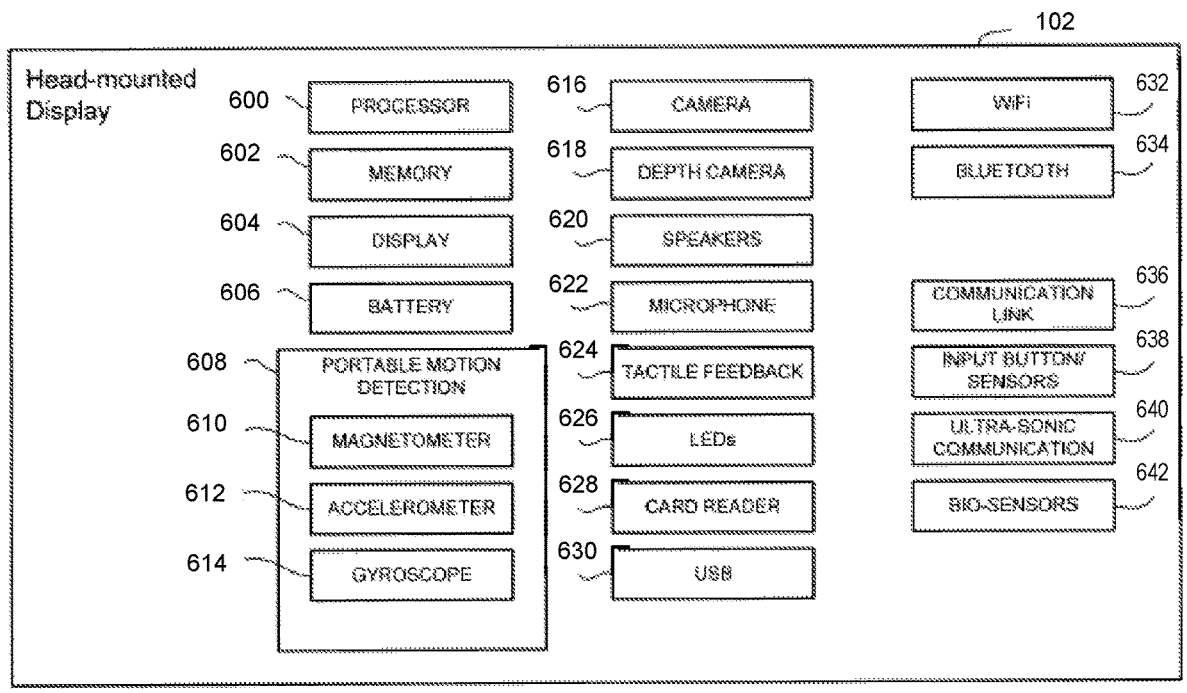
FIG. 6 is a diagram illustrating components of a head-mounted display, in accordance with one embodiment of the disclosure.

FIG. 6, a diagram illustrating components of a head-mounted display (HMD) 102 is shown, in accordance with an embodiment of the disclosure. The HMD may be used during the test phase to collect VR content data and physiological responses of test users when interacting with the test data, or during a classification phase that presents VR content to a user and collects personalized test data related to that user in order to classify that user based on tested discomfort and/or sickness reactions.

The head-mounted display 102 includes a processor 600 for executing program instructions. A memory 602 is provided for storage purposes, and may include both volatile and non-volatile memory. A display 604 is included which provides a visual interface that a user may view. A battery 606 is provided as a power source for the head-mounted display 102. A motion detection module 608 may include any of various kinds of motion sensitive hardware, such as a magnetometer 610, an accelerometer 612, and a gyroscope 614.

An accelerometer is a device for measuring acceleration and gravity induced reaction forces. Single and multiple axis models are available to detect magnitude and direction of the acceleration in different directions. The accelerometer is used to sense inclination, vibration, and shock. In one embodiment, three accelerometers 612 are used to provide the direction of gravity, which gives an absolute reference for two angles (world-space pitch and world-space roll).

A magnetometer measures the strength and direction of the magnetic field in the vicinity of the head-mounted display. In one embodiment, three magnetometers 610 are used within the head-mounted display, ensuring an absolute reference for the world-space yaw angle. In one embodiment, the magnetometer is designed to span the earth magnetic field, which is ±80 microtesla. Magnetometers are affected by metal, and provide a yaw measurement that is monotonic with actual yaw. The magnetic field may be warped due to metal in the environment, which causes a warp in the yaw measurement. If necessary, this warp can be calibrated using information from other sensors such as the gyroscope or the camera. In one embodiment, accelerometer 612 is used together with magnetometer 610 to obtain the inclination and azimuth of the head-mounted display 102.

A gyroscope is a device for measuring or maintaining orientation, based on the principles of angular momentum. In one embodiment, three gyroscopes 614 provide information about movement across the respective axis (x, y and z) based on inertial sensing. The gyroscopes help in detecting fast rotations. However, the gyroscopes can drift overtime without the existence of an absolute reference. This requires resetting the gyroscopes periodically, which can be done using other available information, such as positional/orientation determination based on visual tracking of an object, accelerometer, magnetometer, etc.

A camera 616 is provided for capturing images and image streams of a real environment. More than one camera may be included in the head-mounted display 102, including a camera that is rear-facing (directed away from a user when the user is viewing the display of the head-mounted display 102), and a camera that is front-facing (directed towards the user when the user is viewing the display of the head-mounted display 102). Additionally, a depth camera 618 may be included in the head-mounted display 102 for sensing depth information of objects in a real environment.

In one embodiment, a camera integrated on a front face of the HMD may be used to provide warnings regarding safety. For example, if the user is approaching a wall or object, the user may be warned. In one embodiment, the use may be provided with an outline view of physical objects in the room, to warn the user of their presence. The outline may, for example, be an overlay in the virtual environment. In some embodiments, the HMD user may be provided with a view to a reference marker, that is overlaid in, for example, the floor. For instance, the marker may provide the user a reference of where the center of the room is, which in which the user is playing the game. This may provide, for example, visual information to the user of where the user should move to avoid hitting a wall or other object in the room. Tactile warnings can also be provided to the user, and/or audio warnings, to provide more safety for when the user wears and plays games or navigates content with an HMD.

The head-mounted display 102 includes speakers 620 for providing audio output. Also, a microphone 622 may be included for capturing audio from the real environment, including sounds from the ambient environment, speech made by the user, etc. The head-mounted display 102 includes tactile feedback module 624 for providing tactile feedback to the user. In one embodiment, the tactile feedback module 624 is capable of causing movement and/or vibration of the head-mounted display 102 so as to provide tactile feedback to the user.

LEDs 626 are provided as visual indicators of statuses of the head-mounted display 102. For example, an LED may indicate battery level, power on, etc. A card reader 628 is provided to enable the head-mounted display 102 to read and write information to and from a memory card. A USB interface 630 is included as one example of an interface for enabling connection of peripheral devices, or connection to other devices, such as other portable devices, computers, etc. In various embodiments of the head-mounted display 102, any of various kinds of interfaces may be included to enable greater connectivity of the head-mounted display 102.

A Wi-Fi module 632 is included for enabling connection to the Internet via wireless networking technologies. Also, the head-mounted display 102 includes a Bluetooth module 634 for enabling wireless connection to other devices. A communications link 636 may also be included for connection to other devices. In one embodiment, the communications link 636 utilizes infrared transmission for wireless communication. In other embodiments, the communications link 636 may utilize any of various wireless or wired transmission protocols for communication with other devices.

Input buttons/sensors 638 are included to provide an input interface for the user. Any of various kinds of input interfaces may be included, such as buttons, touchpad, joystick, trackball, etc. An ultra-sonic communication module 640 may be included in head-mounted display 102 for facilitating communication with other devices via ultra-sonic technologies.

Bio-sensors 642 are included to enable detection of physiological data from a user. In one embodiment, the bio-sensors 642 include one or more dry electrodes for detecting bio-electric signals of the user through the user's skin.

The foregoing components of head-mounted display 102 have been described as merely exemplary components that may be included in head-mounted display 102. In various embodiments of the disclosure, the head-mounted display 102 may or may not include some of the various aforementioned components. Embodiments of the head-mounted display 102 may additionally include other components not presently described, but known in the art, for purposes of facilitating aspects of the present disclosure as herein described.

It will be appreciated by those skilled in the art that in various embodiments of the disclosure, the aforementioned handheld device may be utilized in conjunction with an interactive application displayed on a display to provide various interactive functions. The exemplary embodiments described herein are provided by way of example only, and not by way of limitation.

Figure 7:
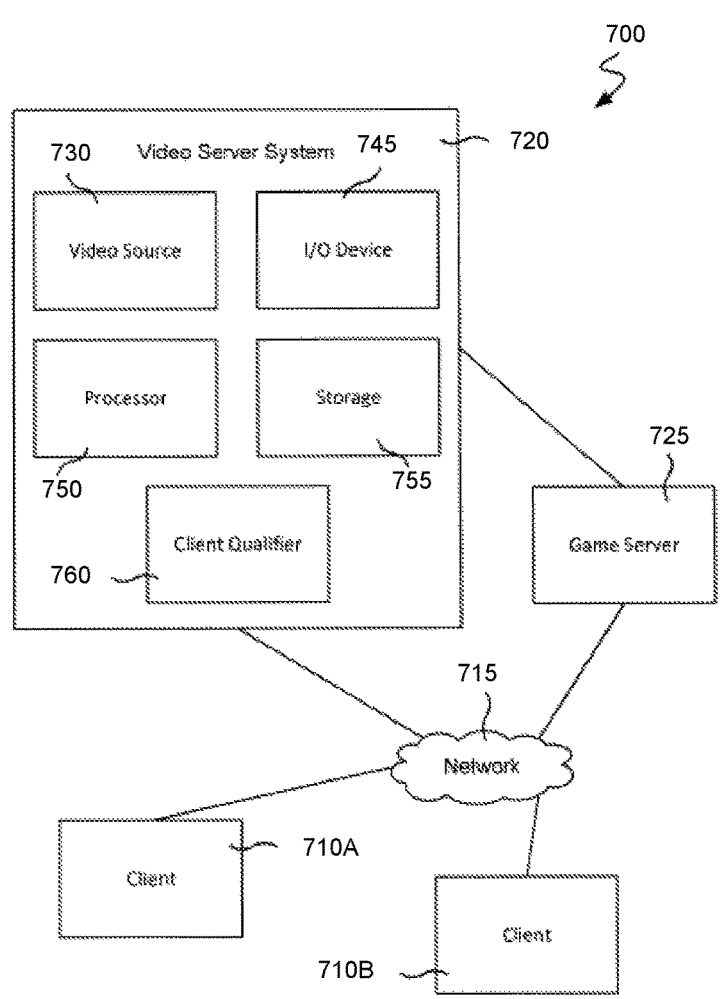
FIG. 7 is a block diagram of Game System, according to various embodiments of the disclosure. Game System is configured to provide a video stream to one or more clients via a network.

FIG. 7 is a block diagram of a Game System 700, according to various embodiments of the disclosure. Game system 700 may be used to provide VR content. Game System 700 is configured to provide a video stream to one or more Clients 710 via a Network 715. Game System 700 typically includes a Video Server System 720 and an optional game server 725. Video Server System 720 is configured to provide the video stream to the one or more Clients 710 with a minimal quality of service. For example, Video Server System 720 may receive a game command that changes the state of or a point of view within a video game, and provide Clients 710 with an updated video stream reflecting this change in state with minimal lag time. The Video Server System 720 may be configured to provide the video stream in a wide variety of alternative video formats, including formats yet to be defined. Further, the video stream may include video frames configured for presentation to a user at a wide variety of frame rates. Typical frame rates are 30 frames per second, 60 frames per second, and 120 frames per second. Although higher or lower frame rates are included in alternative embodiments of the disclosure.

Clients 710, referred to herein individually as 710A., 710B., etc., may include head mounted displays, terminals, personal computers, game consoles, tablet computers, telephones, set top boxes, kiosks, wireless devices, digital pads, stand-alone devices, handheld game playing devices, and/or the like. Typically, Clients 710 are configured to receive encoded video streams (i.e., compressed), decode the video streams, and present the resulting video to a user, e.g., a player of a game. The processes of receiving encoded video streams and/or decoding the video streams typically includes storing individual video frames in a receive buffer of the client. The video streams may be presented to the user on a display integral to Client 710 or on a separate device such as a monitor or television. Clients 710 are optionally configured to support more than one game player. For example, a game console may be configured to support two, three, four or more simultaneous players. Each of these players may receive a separate video stream, or a single video stream may include regions of a frame generated specifically for each player, e.g., generated based on each player's point of view. Clients 710 are optionally geographically dispersed. The number of clients included in Game System 700 may vary widely from one or two to thousands, tens of thousands, or more. As used herein, the term "game player" is used to refer to a person that plays a game and the term "game playing device" is used to refer to a device used to play a game. In some embodiments, the game playing device may refer to a plurality of computing devices that cooperate to deliver a game experience to the user. For example, a game console and an HMD may cooperate with the video server system 720 to deliver a game viewed through the HMD. In one embodiment, the game console receives the video stream from the video server system 720, and the game console forwards the video stream, or updates to the video stream, to the HMD for rendering.

Clients 710 are configured to receive video streams via Network 715. Network 715 may be any type of communication network including, a telephone network, the Internet, wireless networks, powerline networks, local area networks, wide area networks, private networks, and/or the like. In typical embodiments, the video streams are communicated via standard protocols, such as TCP/IP or UDP/IP. Alternatively, the video streams are communicated via proprietary standards.

A typical example of Clients 710 is a personal computer comprising a processor, non-volatile memory, a display, decoding logic, network communication capabilities, and input devices. The decoding logic may include hardware, firmware, and/or software stored on a computer readable medium. Systems for decoding (and encoding) video streams are well known in the art and vary depending on the particular encoding scheme used.

Clients 710 may, but are not required to, further include systems configured for modifying received video. For example, a client may be configured to perform further rendering, to overlay one video image on another video image, to crop a video image, and/or the like. For example, Clients 710 may be configured to receive various types of video frames, such as I-frames, P-frames and B-frames, and to process these frames into images for display to a user. In some embodiments, a member of Clients 710 is configured to perform further rendering, shading, conversion to 3-D, or like operations on the video stream. A member of Clients 710 is optionally configured to receive more than one audio or video stream. Input devices of Clients 710 may include, for example, a one-hand game controller, a two-hand game controller, a gesture recognition system, a gaze recognition system, a voice recognition system, a keyboard, a joystick, a pointing device, a force feedback device, a motion and/or location sensing device, a mouse, a touch screen, a neural interface, a camera, input devices yet to be developed, and/or the like.

The video stream (and optionally audio stream) received by Clients 710 is generated and provided by Video Server System 720. As is described further elsewhere herein, this video stream includes video frames (and the audio stream includes audio frames). The video frames are configured (e.g., they include pixel information in an appropriate data structure) to contribute meaningfully to the images displayed to the user. As used herein, the term "video frames" is used to refer to frames including predominantly information that is configured to contribute to, e.g. to effect, the images shown to the user. Most of the teachings herein with regard to "video frames" can also be applied to "audio frames."

Clients 710 are typically configured to receive inputs from a user. These inputs may include game commands configured to change the state of the video game or otherwise affect gameplay. The game commands can be received using input devices and/or may be automatically generated by computing instructions executing on Clients 710. The received game commands are communicated from Clients 710 via Network 715 to Video Server System 720 and/or Game Server 725. For example, in some embodiments, the game commands are communicated to Game Server 725 via Video Server System 720. In some embodiments, separate copies of the game commands are communicated from Clients 710 to Game Server 725 and Video Server System 720. The communication of game commands is optionally dependent on the identity of the command Game commands are optionally communicated from Client 710A through a different route or communication channel that that used to provide audio or video streams to Client 710A.

Game Server 725 is optionally operated by a different entity than Video Server System 720. For example, Game Server 725 may be operated by the publisher of a multiplayer game. In this example, Video Server System 720 is optionally viewed as a client by Game Server 725 and optionally configured to appear from the point of view of Game Server 725 to be a prior art client executing a prior art game engine. Communication between Video Server System 720 and Game Server 725 optionally occurs via Network 715. As such, Game Server 725 can be a prior art multiplayer game server that sends game state information to multiple clients, one of which is game server system 720. Video Server System 720 may be configured to communicate with multiple instances of Game Server 725 at the same time. For example, Video Server System 720 can be configured to provide a plurality of different video games to different users. Each of these different video games may be supported by a different Game Server 725 and/or published by different entities. In some embodiments, several geographically distributed instances of Video Server System 720 are configured to provide game video to a plurality of different users. Each of these instances of Video Server System 720 may be in communication with the same instance of Game Server 725. Communication between Video Server System 720 and one or more Game Server 725 optionally occurs via a dedicated communication channel. For example, Video Server System 720 may be connected to Game Server 725 via a high bandwidth channel that is dedicated to communication between these two systems.

Video Server System 720 comprises at least a Video Source 730, an I/O Device 745, a Processor 750, and non-transitory Storage 755. Video Server System 720 may include one computing device or be distributed among a plurality of computing devices. These computing devices are optionally connected via a communications system such as a local area network.

Video Source 730 is configured to provide a video stream, e.g., streaming video or a series of video frames that form a moving picture. In some embodiments, Video Source 730 includes a video game engine and rendering logic. The video game engine is configured to receive game commands from a player and to maintain a copy of the state of the video game based on the received commands. This game state includes the position of objects in a game environment, as well as typically a point of view. The game state may also include properties, images, colors and/or textures of objects.

The game state is typically maintained based on game rules, as well as game commands such as move, turn, attack, set focus to, interact, use, and/or the like. Part of the game engine is optionally disposed within Game Server 725. Game Server 725 may maintain a copy of the state of the game based on game commands received from multiple players using geographically disperse clients. In these cases, the game state is provided by Game Server 725 to Video Source 730, wherein a copy of the game state is stored and rendering is performed. Game Server 725 may receive game commands directly from Clients 710 via Network 715, and/or may receive game commands via Video Server System 720.

Video Source 730 typically includes rendering logic, e.g., hardware, firmware, and/or software stored on a computer readable medium such as Storage 755. This rendering logic is configured to create video frames of the video stream based on the game state. All or part of the rendering logic is optionally disposed within a graphics processing unit (GPU). Rendering logic typically includes processing stages configured for determining the three-dimensional spatial relationships between objects and/or for applying appropriate textures, etc., based on the game state and viewpoint. The rendering logic produces raw video that is then usually encoded prior to communication to Clients 710. For example, the raw video may be encoded according to an Adobe Flash® standard, .wav, H.264, H.263, On2, VP6, VC-1, WMA, Huffyuv, Lagarith, MPG-x, Xvid, FFmpeg, x264, VP6-8, realvideo, mp3, or the like. The encoding process produces a video stream that is optionally packaged for delivery to a decoder on a remote device. The video stream is characterized by a frame size and a frame rate. Typical frame sizes include 800×600, 1280×720 (e.g., 720 p), 1024×768, although any other frame sizes may be used. The frame rate is the number of video frames per second. A video stream may include different types of video frames. For example, the H.264 standard includes a "P" frame and a "I" frame. I-frames include information to refresh all macro blocks/pixels on a display device, while P-frames include information to refresh a subset thereof. P-frames are typically smaller in data size than are I-frames. As used herein the term "frame size" is meant to refer to a number of pixels within a frame. The term "frame data size" is used to refer to a number of bytes required to store the frame.

In alternative embodiments Video Source 730 includes a video recording device such as a camera. This camera may be used to generate delayed or live video that can be included in the video stream of a computer game. The resulting video stream optionally includes both rendered images and images recorded using a still or video camera. Video Source 730 may also include storage devices configured to store previously recorded video to be included in a video stream. Video Source 730 may also include motion or positioning sensing devices configured to detect motion or position of an object, e.g., person, and logic configured to determine a game state or produce video-based on the detected motion and/or position.

Video Source 730 is optionally configured to provide overlays configured to be placed on other video. For example, these overlays may include a command interface, log in instructions, messages to a game player, images of other game players, video feeds of other game players (e.g., webcam video). In embodiments of Client 710A including a touch screen interface or a gaze detection interface, the overlay may include a virtual keyboard, joystick, touch pad, and/or the like. In one example of an overlay a player's voice is overlaid on an audio stream. Video Source 730 optionally further includes one or more audio sources.

In embodiments wherein Video Server System 720 is configured to maintain the game state based on input from more than one player, each player may have a different point of view comprising a position and direction of view. Video Source 730 is optionally configured to provide a separate video stream for each player based on their point of view. Further, Video Source 730 may be configured to provide a different frame size, frame data size, and/or encoding to each of Client 710. Video Source 730 is optionally configured to provide 3-D video and/or immersive 360 degree encoded video.

I/O Device 745 is configured for Video Server System 720 to send and/or receive information such as video, commands, requests for information, a game state, gaze information, device motion, device location, user motion, client identities, player identities, game commands, security information, audio, and/or the like. I/O Device 745 typically includes communication hardware such as a network card or modem. I/O Device 745 is configured to communicate with Game Server 725, Network 715, and/or Clients 710.

Processor 750 is configured to execute logic, e.g. software, included within the various components of Video Server System 720 discussed herein. For example, Processor 750 may be programmed with software instructions in order to perform the functions of Video Source 730, Game Server 725, and/or a Client Qualifier 760. Video Server System 720 optionally includes more than one instance of Processor 750. Processor 750 may also be programmed with software instructions in order to execute commands received by Video Server System 720, or to coordinate the operation of the various elements of Game System 700 discussed herein. Processor 750 may include one or more hardware device. Processor 750 is an electronic processor.

Storage 755 includes non-transitory analog and/or digital storage devices. For example, Storage 755 may include an analog storage device configured to store video frames. Storage 755 may include a computer readable digital storage, e.g., a hard drive, an optical drive, or solid state storage. Storage 715 is configured (e.g., by way of an appropriate data structure or file system) to store video frames, artificial frames, a video stream including both video frames and artificial frames, audio frame, an audio stream, and/or the like. Storage 755 is optionally distributed among a plurality of devices. In some embodiments, Storage 755 is configured to store the software components of Video Source 730 discussed elsewhere herein. These components may be stored in a format ready to be provisioned when needed.

Video Server System 720 optionally further comprises Client Qualifier 760. Client Qualifier 760 is configured for remotely determining the capabilities of a client, such as Clients 710A or 710B. These capabilities can include both the capabilities of Client 710A itself as well as the capabilities of one or more communication channels between Client 710A and Video Server System 720. For example, Client Qualifier 760 may be configured to test a communication channel through Network 715.

Client Qualifier 760 can determine (e.g., discover) the capabilities of Client 710A manually or automatically. Manual determination includes communicating with a user of Client 710A and asking the user to provide capabilities. For example, in some embodiments, Client Qualifier 760 is configured to display images, text, and/or the like within a browser of Client 710A. In one embodiment, Client 710A is an HMD that includes a browser. In another embodiment, client 710A is a game console having a browser, which may be displayed on the HMD. The displayed objects request that the user enter information such as operating system, processor, video decoder type, type of network connection, display resolution, etc. of Client 710A. The information entered by the user is communicated back to Client Qualifier 760.

Automatic determination may occur, for example, by execution of an agent on Client 710A and/or by sending test video to Client 710A. The agent may comprise computing instructions, such as java script, embedded in a web page or installed as an add-on. The agent is optionally provided by Client Qualifier 760. In various embodiments, the agent can find out processing power of Client 710A, decoding and display capabilities of Client 710A, lag time reliability and bandwidth of communication channels between Client 710A and Video Server System 720, a display type of Client 710A, firewalls present on Client 710A, hardware of Client 710A, software executing on Client 710A, registry entries within Client 710A, and/or the like.

Client Qualifier 760 includes hardware, firmware, and/or software stored on a computer readable medium. Client Qualifier 760 is optionally disposed on a computing device separate from one or more other elements of Video Server System 720. For example, in some embodiments, Client Qualifier 760 is configured to determine the characteristics of communication channels between Clients 710 and more than one instance of Video Server System 720. In these embodiments the information discovered by Client Qualifier can be used to determine which instance of Video Server System 720 is best suited for delivery of streaming video to one of Clients 710.

The following applications provide information on HMDs and motion sickness, including: commonly assigned, co-pending U.S. patent application Ser. No. 14/206,219, entitled "SWITCHING MODE OF OPERATION IN A HEAD MOUNTED DISPLAY," filed on Mar. 12, 2014; commonly assigned, co-pending U.S. patent application Ser. No. 14/712,575, entitled "SENSORY STIMULUS MANAGEMENT IN HEAD MOUNTED DISPLAY," filed on May 14, 2015; commonly assigned, co-pending U.S. patent application Ser. No. 14/615,115, entitled "MOTION SICKNESS MONITORING AND APPLICATION OF SUPPLEMENTAL SOUND TO COUNTERACT SICKNESS," filed on Feb. 5, 2015; and commonly assigned, co-pending U.S. patent application Ser. No. 14/627,406, entitled "SCANNING DISPLAY SYSTEM IN HEAD-MOUNTED DISPLAY FOR VIRTUAL REALITY," filed on Feb. 20, 2015; all of which are hereby incorporated by reference in its entirety. More information on the deep learning process implemented in some embodiments of the present invention is provided in "Introduction to Machine Learning," Second Edition, Ethem Alpaydin, Massachusetts Institute of Technology, 2010, which is hereby incorporated by reference in its entirety.

While specific embodiments have been provided for building models configured to recognize which VR content induces user discomfort and/or sickness, to classify VR content based on predicted user discomfort and/or sickness, and for classifying users based on tested responses of user discomfort and/or sickness when viewing VR content, these are described by way of example and not by way of limitation. Those skilled in the art having read the present disclosure will realize additional embodiments falling within the spirit and scope of the present disclosure.

It should be understood that the various embodiments defined herein may be combined or assembled into specific implementations using the various features disclosed herein. Thus, the examples provided are just some possible examples, without limitation to the various implementations that are possible by combining the various elements to define many more implementations. In some examples, some implementations may include fewer elements, without departing from the spirit of the disclosed or equivalent implementations.

Embodiments of the present disclosure may be practiced with various computer system configurations including hand-held devices, microprocessor systems, microprocessor-based or programmable consumer electronics, minicomputers, mainframe computers and the like. Embodiments of the present disclosure can also be practiced in distributed computing environments where tasks are performed by remote processing devices that are linked through a wire-based or wireless network.

With the above embodiments in mind, it should be understood that embodiments of the present disclosure can employ various computer-implemented operations involving data stored in computer systems. These operations are those requiring physical manipulation of physical quantities. Any of the operations described herein that form part of embodiments of the present disclosure are useful machine operations. Embodiments of the invention also relate to a device or an apparatus for performing these operations. The apparatus can be specially constructed for the required purpose, or the apparatus can be a general-purpose computer selectively activated or configured by a computer program stored in the computer. In particular, various general-purpose machines can be used with computer programs written in accordance with the teachings herein, or it may be more convenient to construct a more specialized apparatus to perform the required operations.

The disclosure can also be embodied as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing disclosure has been described in some detail for purposes of clarity of understanding, it will be apparent that certain changes and modifications can be practiced within the scope of the appended claims. Accordingly, the present embodiments are to be considered as illustrative and not restrictive, and embodiments of the present disclosure is not to be limited to the details given herein, but may be modified within the scope and equivalents of the appended claims.

What is claimed is:

1. A method for classification of content for use in head mounted displays (HMDs), comprising:
  accessing a model that identifies a plurality of learned patterns associated with baseline virtual reality (VR) content that is likely to cause discomfort, the baseline VR content including a first plurality of images;
  executing a video game application under simulation that is automated to generate VR content including a second plurality of images, the executing of the video game application being controlled by simulated user interaction that is automated;
  extracting data based on the VR content;
  comparing the data to the model to identify a pattern in the data that correlates to a learned pattern from the model likely to cause discomfort, wherein the pattern in the data includes sequential images in the VR content and simulated controller inputs that corresponds to the learned pattern including sequential baseline images of the baseline VR content and controller inputs;
  identifying a point in a progression through the video game application corresponding to the pattern that includes the sequential images in the VR content and the simulated controller inputs;

identifying a section of code in the video game application corresponding to the point that is identified; and generating a flag indicating that the section of code corresponds to the point in the progression through the video game application that correlates to the learned pattern that is likely to cause discomfort.

2. The method of claim 1, further comprising:

determining a level of discomfort for the VR content based on the model, wherein the model predicts the level of discomfort experienced by a prospective user when interacting with the VR content; and assigning a discomfort classification for the VR content based on the level of discomfort that is determined.

3. The method of claim 2, further comprising:

provide notification of the discomfort classification to the prospective user.

4. The method of claim 2, further comprising:

comparing the level of discomfort that is determined to a targeted level of discomfort designed for the VR content; and providing notification of a mismatch when the level of discomfort that is determined does not satisfy the targeted level of discomfort.

5. The method of claim 4, further comprising:

providing a recommendation to change the video game application when there is the mismatch.

6. The method of claim 1, wherein the pattern that is identified includes a pattern of actions from simulated user interaction used to control the executing of the video game application.

7. The method of claim 2, wherein the discomfort classification is taken from a group of discomfort classifications including a first classification level indicating high discomfort and a second classification level indicating low or no discomfort.

8. The method of claim 1, further comprising:

executing a plurality of testing video game applications for interaction by a plurality of testers to generate the baseline VR content;

extracting data associated with tester interactions with the baseline VR content, the data that is extracted in association with the tester interactions generated during execution of the plurality of testing video game applications;

monitoring physiological measurements of the plurality of testers when interacting with the baseline VR content, wherein the baseline VR content is associated with a plurality of baseline discomfort reactions of the plurality of testers, wherein known patterns of physiological measurements are associated with expected discomfort reactions;

applying the physiological measurements and the data associated with the tester interactions that is extracted to a deep learning engine to generate the model; and building the model by correlating the physiological measurements and the data that is associated with the tester interactions that is extracted to determine the plurality of learned patterns that is likely to cause the discomfort based on a set of physiological measurements that align with the plurality of baseline discomfort reactions of the plurality of testers.

9. The method of claim 8, wherein the physiological measurements include at least one of electrogastrography, galvanic skin resistance, alpha wave, heart rate, eye gaze, and head motion.

10. The method of claim 1, further comprising:

classifying at least one point in the video game application associated with at least one of one or more patterns that are identified and that are likely to cause the discomfort.

11. A method for classification of content for use in head mounted displays (HMDs), comprising:

executing a plurality of testing video game applications for interaction by a plurality of testers to generate a plurality of baseline virtual reality (VR) content including a first plurality of images;

extracting testing data associated with tester interactions with the plurality of baseline VR content, the testing data that is extracted being generated during execution of the plurality of testing video game applications;

monitoring physiological measurements of the plurality of testers when interacting with the plurality of baseline VR content, wherein the plurality of baseline VR content is associated with a plurality of baseline discomfort reactions of the plurality of testers, wherein known patterns of physiological measurements are associated with expected discomfort reactions;

applying the physiological measurements and the testing data that is extracted to a deep learning engine;

determining a plurality of learned patterns associated with the plurality of baseline VR content, wherein the plurality of learned patterns is likely to produce discomfort experiences in the plurality of testers based on a set of physiological measurements that align with the plurality of baseline discomfort reactions of the plurality of testers, wherein a learned pattern in the plurality of learned patterns includes sequential baseline images in the plurality of baseline VR content and controller inputs;

correlating a pattern including sequential images and simulated controller inputs that is automated of a video game application to the learned pattern;

identifying a point in a progression through the video game application corresponding to the pattern that includes the sequential images and the simulated controller inputs;

identifying a section of code in the video game application corresponding to the point that is identified; and generating a flag indicating that the section of code in the video game application corresponds to the point in the progression through the video game application that correlates to the learned pattern that is likely to cause discomfort.

12. The method of claim 11, further comprising:

building a model that identifies the plurality of learned patterns associated with generation of corresponding baseline VR content that is likely to cause the discomfort experiences in the plurality of testers.

13. The method of claim 11, wherein one of the plurality of learned patterns includes a pattern of actions taken by one or more testers during the execution of the plurality of testing video game applications.

14. The method of claim 12, further comprising:

accessing the model that identifies the plurality of learned patterns associated with the generation of corresponding baseline VR content that is likely to cause the discomfort experiences in the plurality of testers;

executing the video game application under simulation to generate VR content including a second plurality of images;

extracting data based on the VR content, the data that is extracted being generated during execution of the video game application under simulation; and comparing the data that is extracted to the model to identify one or more patterns in the data that is extracted matching at least one of the learned patterns from the model and determining that the one or more patterns that are identified are likely to cause discomfort based on the matching, wherein an identified pattern from the one or more patterns that are identified includes a pattern of second sequential images in the VR content and second simulated controller inputs used for generating the pattern of sequential images that matches the learned pattern including the pattern of sequential baseline images of the plurality of baseline VR content and the controller inputs used for generating the pattern of sequential baseline images.

15. The method of claim 14, further comprising:

determining a level of discomfort for the VR content based on the model, wherein the model predicts the level of discomfort experienced by a prospective user when interacting with the VR content; and assigning a discomfort classification for the VR content based on the level of discomfort that is determined.

16. A method for classification of content for use head mounted displays (HMDs), comprising:

accessing a model that identifies a plurality of learned patterns associated with baseline virtual reality (VR) content that is likely to cause discomfort, the baseline VR content including a first plurality of images;

processing a video game application under simulation that is automated to generate data based on VR content of the video game application being processed, the VR content including a second plurality of images, the processing of the video game application being controlled by simulated user interaction that is automated; and comparing the data to the model to identify a pattern in the data that correlates to a learned pattern from the model likely to cause discomfort, wherein the pattern includes sequential images in the VR content and simulated controller inputs that corresponds to the learned pattern including sequential baseline images of the baseline VR content and controller inputs;

identifying a point in a progression through the video game application corresponding to the pattern that includes the sequential images in the VR content and the simulated controller inputs;

identifying a section of code in the video game application corresponding to the point that is identified; and generating a flag indicating that the section of code corresponds to the point in the progression through the video game that correlates to the learned pattern that is likely to cause discomfort.

17. The method of claim 16, wherein the processing the video game application includes:

executing the video game application to generate the VR content; and wherein the data that is generated includes the simulated user interaction.

18. The method of claim 16, further comprising:

determining a level of discomfort for the VR content based on the model, wherein the model predicts the level of discomfort experienced by a prospective user when interacting with the VR content; and assigning a discomfort classification for the VR content based on the level of discomfort that is determined.

19. The method of claim 16, further comprising:

classifying at least one point in the video game application associated with the pattern that is identified that is likely to cause the discomfort.

* * * * *